US012797326B2

(12) United States Patent
Lim et al.

(10) Patent No.: US 12,797,326 B2
(45) Date of Patent: Nov. 17, 2026

(54) COSMETIC COMPOSITION COMPRISING FERMENTED CHESTNUT HUSK EXTRACT OR FRACTION THEREOF AS ACTIVE INGREDIENT

(71) Applicant: KOREA UNIVERSITY RESEARCH AND BUSINESS FOUNDATION, Seoul (KR)

(72) Inventors: Seung Taik Lim, Seoul (KR); Nuntinee Ritthibut, Chiang Mai (TH); Yingyu Jin, Seoul (KR); Su Jin Oh, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 605 days.

(21) Appl. No.: 17/928,326

(22) PCT Filed: Jun. 10, 2021

(86) PCT No.: PCT/KR2021/007239

§ 371 (c)(1),
(2) Date: Nov. 29, 2022

(87) PCT Pub. No.: WO2021/256773

PCT Pub. Date: Dec. 23, 2021

(65) Prior Publication Data

US 2023/0104900 A1 Apr. 6, 2023

(30) Foreign Application Priority Data

Jun. 19, 2020 (KR) ........................ 10-2020-0074885
Jun. 9, 2021 (KR) ........................ 10-2021-0074719

(51) Int. Cl.
*A61K 8/9789* (2017.01)
*A61Q 19/02* (2006.01)
*A61Q 19/08* (2006.01)

(52) U.S. Cl.
CPC ............ *A61K 8/9789* (2017.08); *A61Q 19/02* (2013.01); *A61Q 19/08* (2013.01); *A61K 2800/85* (2013.01)

(58) Field of Classification Search
None
See application file for complete search history.

(56) References Cited

FOREIGN PATENT DOCUMENTS

| | | | | | |
|---|---|---|---|---|---|
| CN | 103976203 | A | * | 8/2014 | ........... A23L 33/105 |
| CN | 105852012 | | * | 8/2016 | |
| CN | 105852012 | A | | 8/2016 | |
| JP | 2004-352634 | A | | 12/2004 | |
| JP | 2014088360 | A | * | 5/2014 | |
| KR | 890005252 | B1 | * | 12/1989 | ............ A23L 33/00 |
| KR | 10-0308178 | B1 | | 2/2002 | |
| KR | 10-2014-0062456 | A | | 5/2014 | |
| KR | 10-2016-0072382 | A | | 6/2016 | |
| KR | 10-2016-0096323 | A | | 8/2016 | |
| KR | 10-1980142 | B1 | | 5/2019 | |
| KR | 10-2019-0102364 | A | | 9/2019 | |
| KR | 10-2024-0103439 | A | | 7/2024 | |
| WO | WO-2014104171 | A1 | * | 7/2014 | ................ A61P 3/10 |

OTHER PUBLICATIONS

English Translation of Kr 20160072382A (Year: 2016).*
English Translation of JP 2014088260 (Year: 2014).*
English Translation of KR-890005252-B1, Published Dec. 20, 1989.*
English Translation of CN-103976203-A, published Aug. 13, 2014.*
International Search Report issued on Oct. 7, 2021, in corresponding PCT/KR2021/007239 (3 pages in Korean).
Gu, Yul Ri, et al., "The Anti-Oxidant, Whitening and Anti-Wrinkle Effects of *Castanea crenata* Inner Shell Extracts Processed by Enzyme Treatment and Pressurized Extraction", The Korean Society of Food Preservation, Jan. 26, 2028, (p. 79-89).
Korean Office Action Issued on Nov. 26, 2022, in Counterpart Korean Patent Application No. 10-2021-0074719 (8 Pages in Korean).
Korean Office Action Issued on Jan. 22, 2024, in Counterpart Korean Patent Application No. 10-2021-0074719 (7 Pages in Korean).
Chinese Office Action Issued on Jan. 23, 2025, in Counterpart Chinese Patent Application No. 202180043463.4 (6 Pages in Chinese).

* cited by examiner

*Primary Examiner* — David J Blanchard
*Assistant Examiner* — Sarah J Chickos
(74) *Attorney, Agent, or Firm* — NSIP Law

(57) ABSTRACT

The present invention relates to a cosmetic composition comprising a fermented chestnut husk extract or a fraction thereof as an active ingredient. The fermented chestnut husk extract or fraction thereof according to the present invention can be used to provide a cosmetic composition that exhibits an increased total phenolic content, high antioxidative activity, and excellent skin whitening and wrinkle reduction due to the fermentation, extraction, and fractionation processes thereof.

12 Claims, 28 Drawing Sheets

[Fig. 1A]
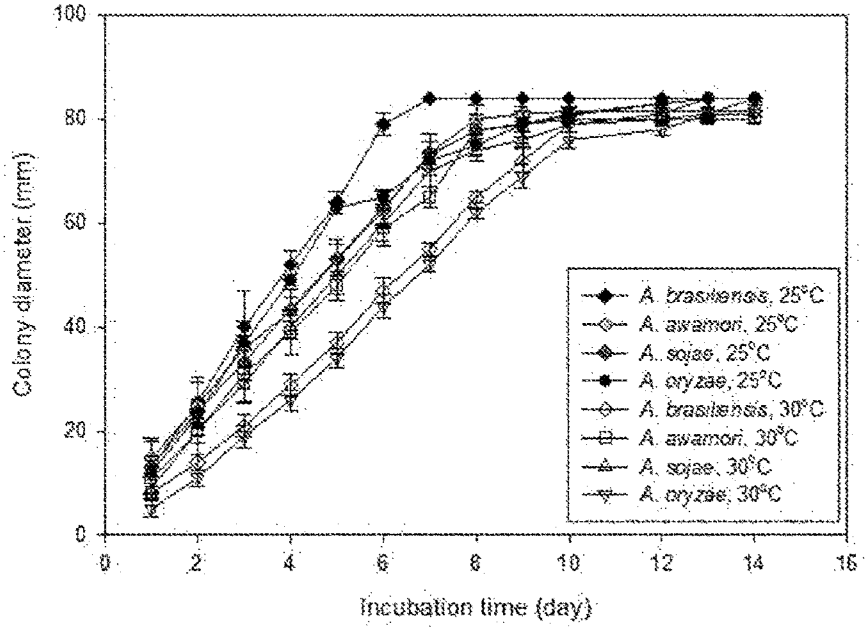
[Fig. 1B]
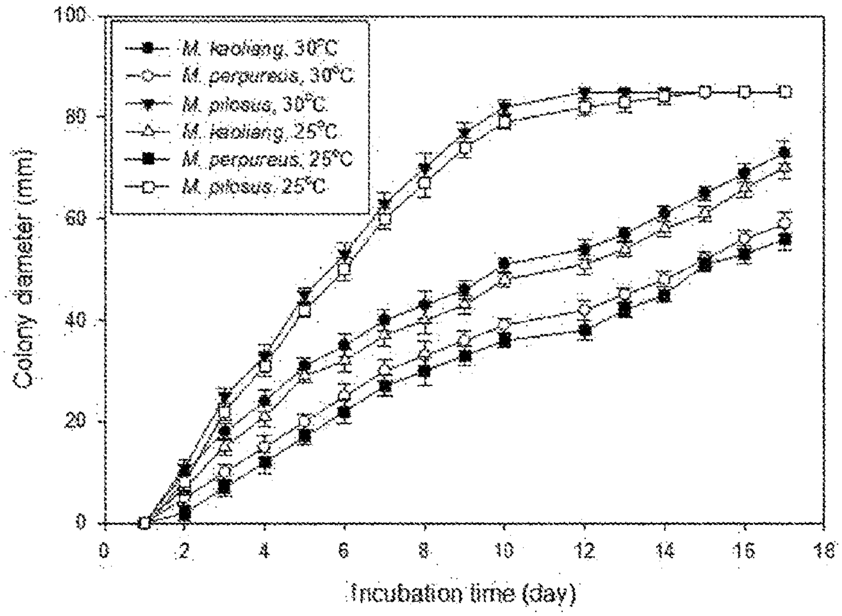

[Fig. 2A]
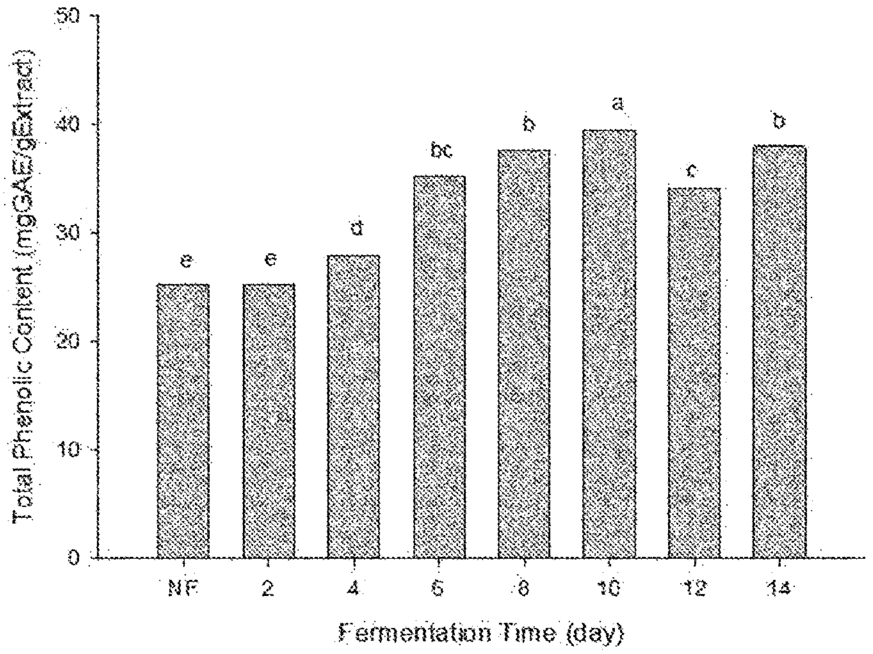
[Fig. 2B]
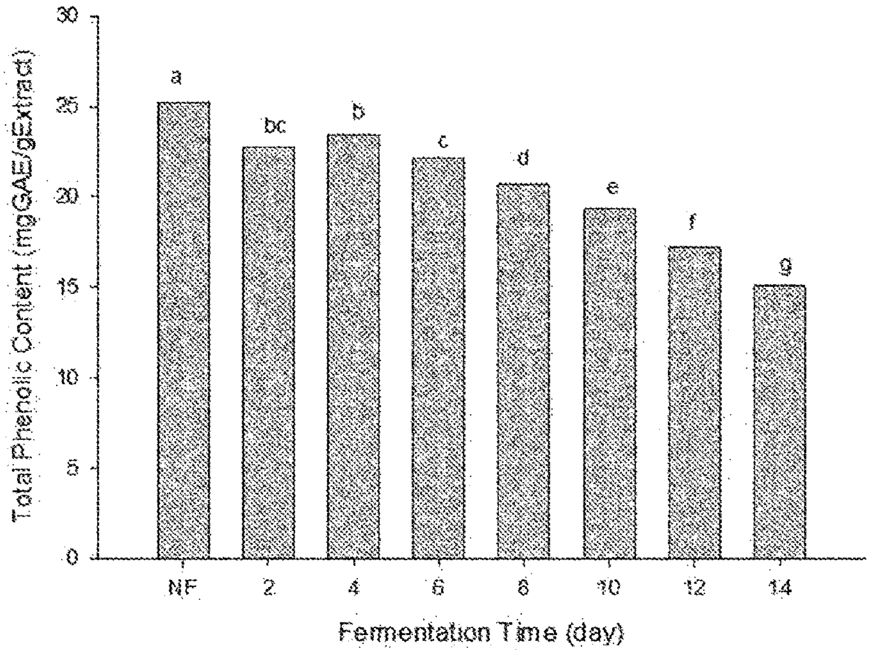

[Fig. 2C]
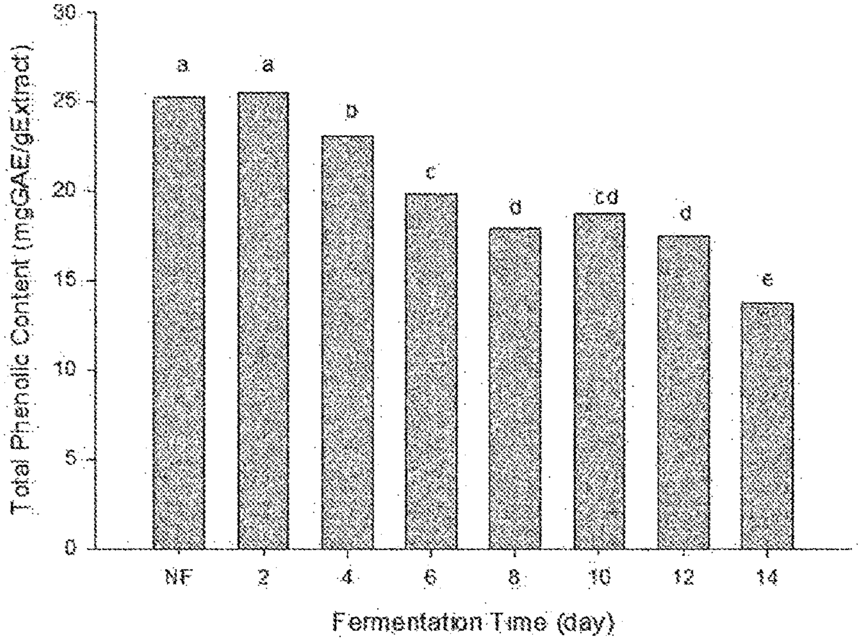
[Fig. 2D]
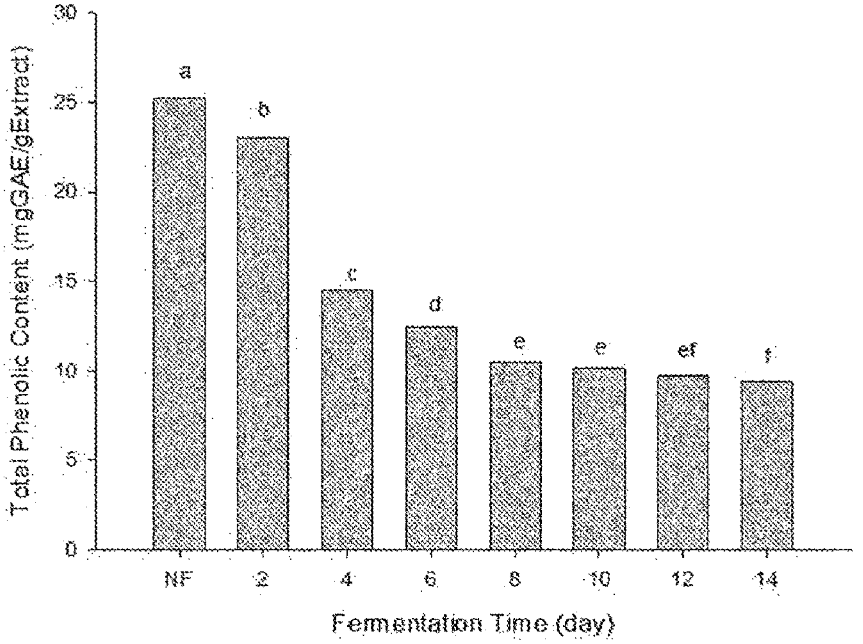

[Fig. 3A]
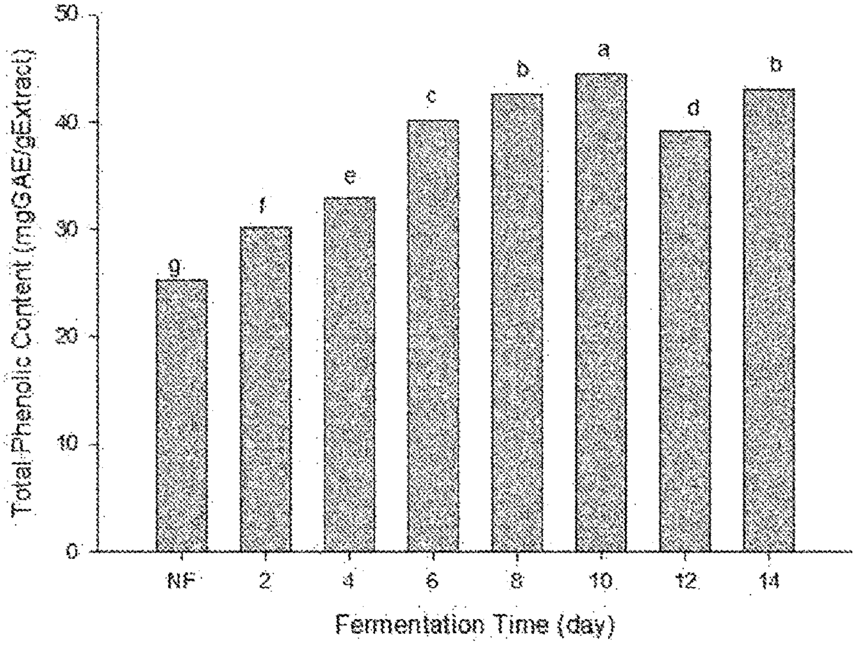
[Fig. 3B]
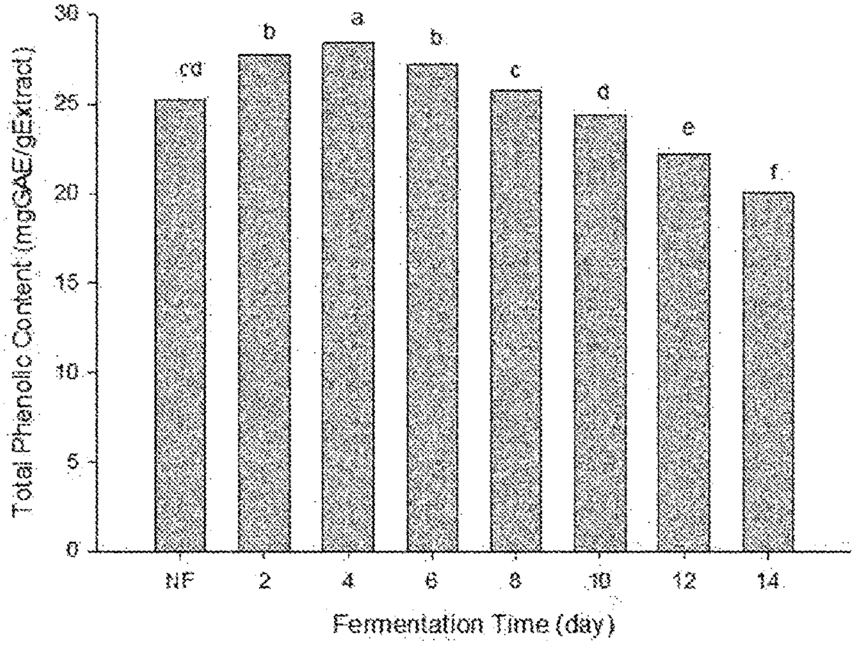

[Fig. 3C]
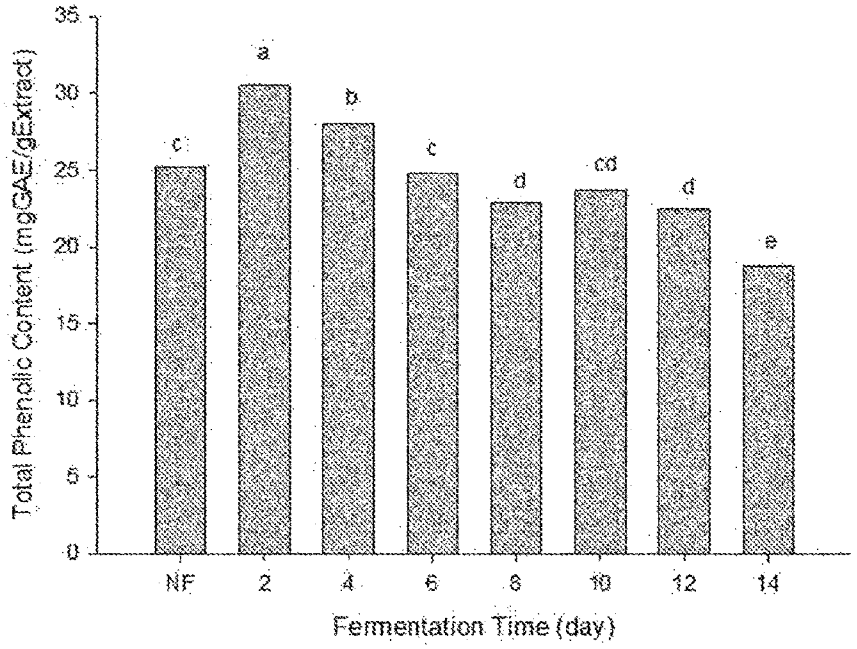
[Fig. 3D]
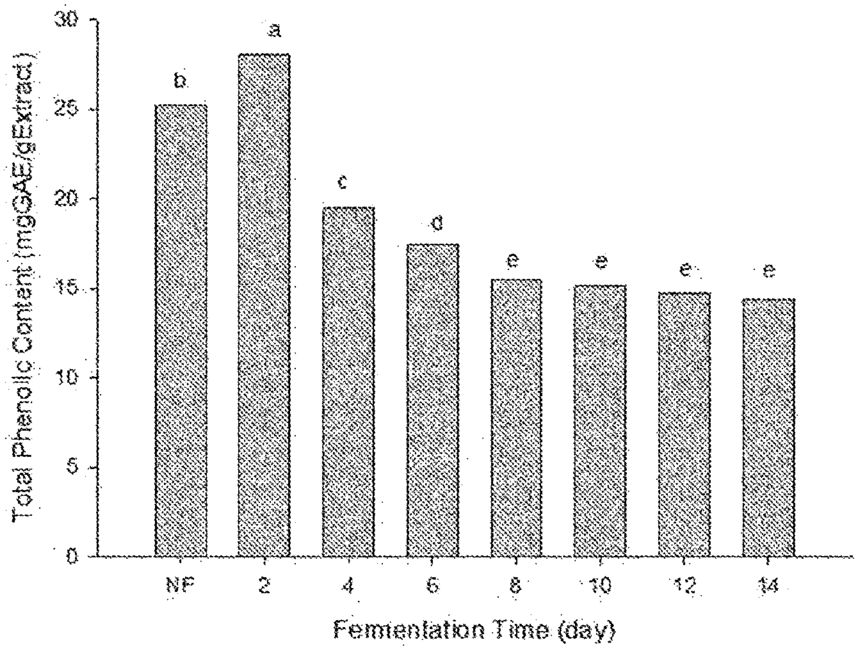

[Fig. 4A]
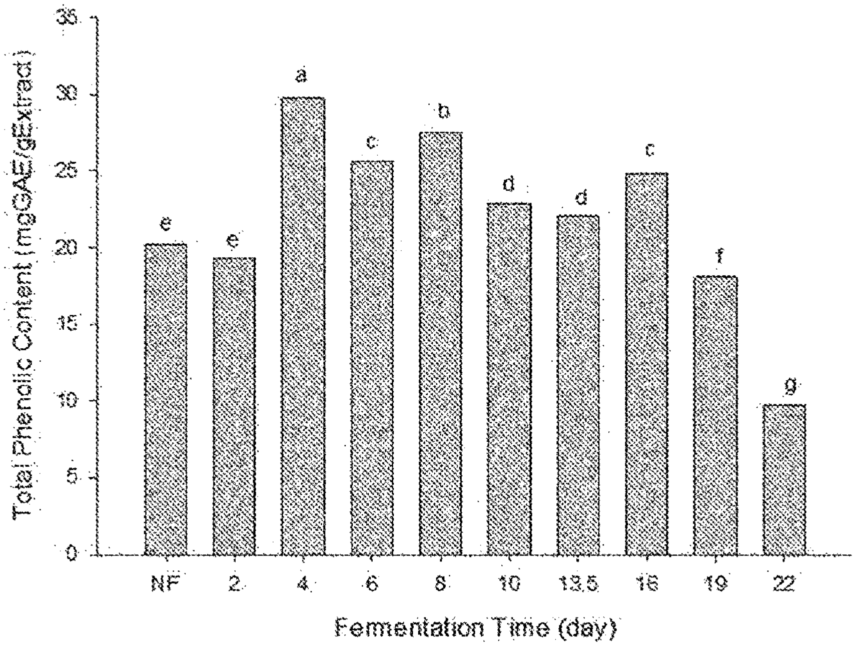
[Fig. 4B]
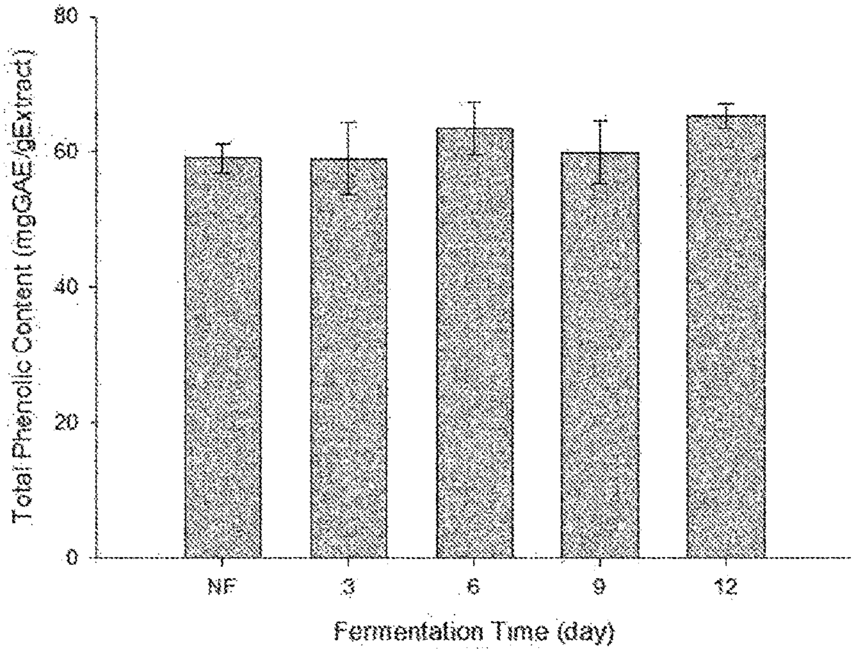

[Fig. 4C]
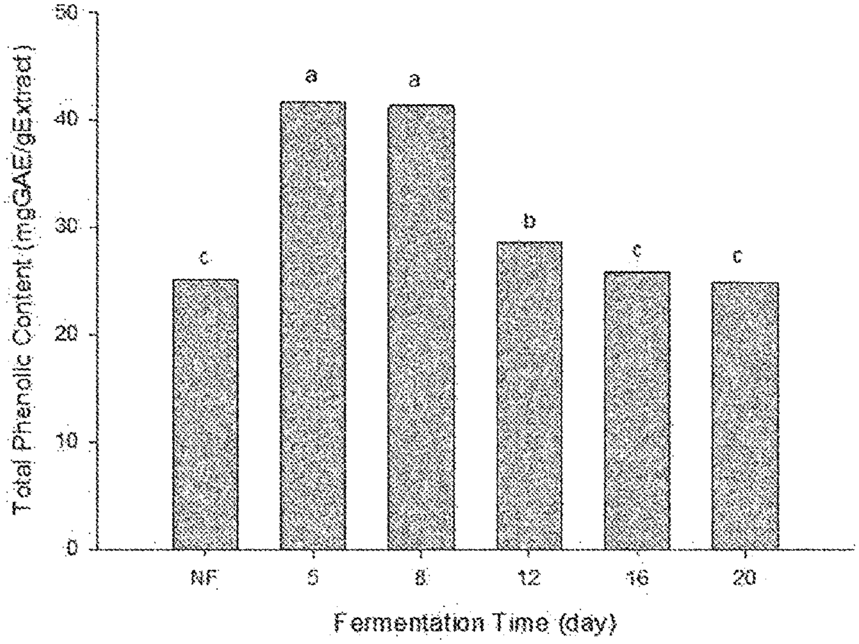
[Fig. 5A]
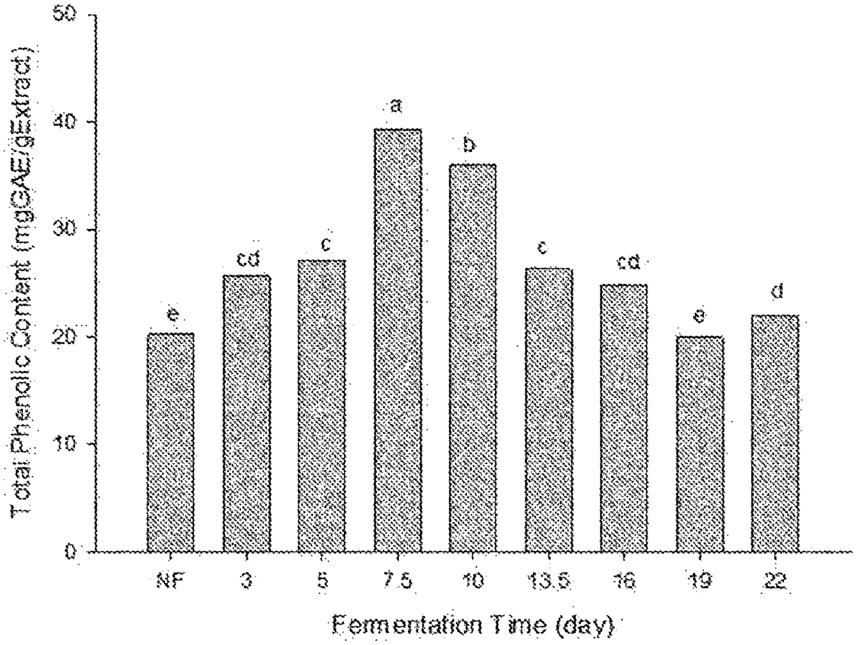

[Fig. 5B]
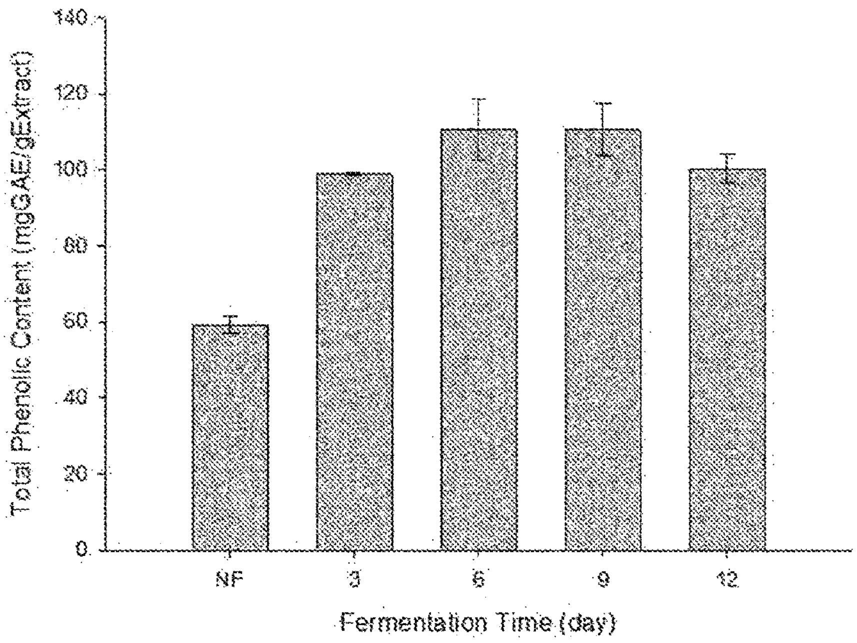
[Fig. 5C]
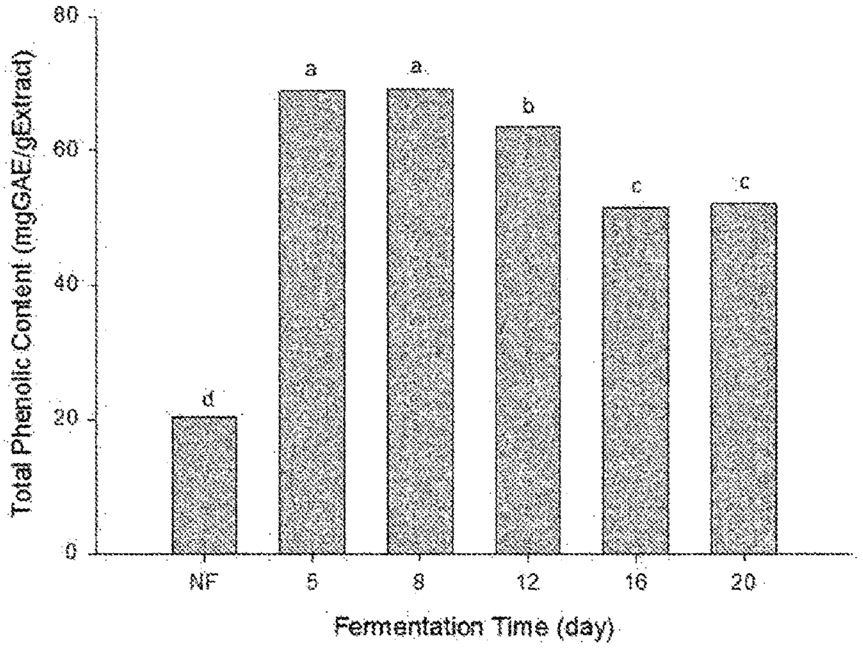

[Fig. 6A]
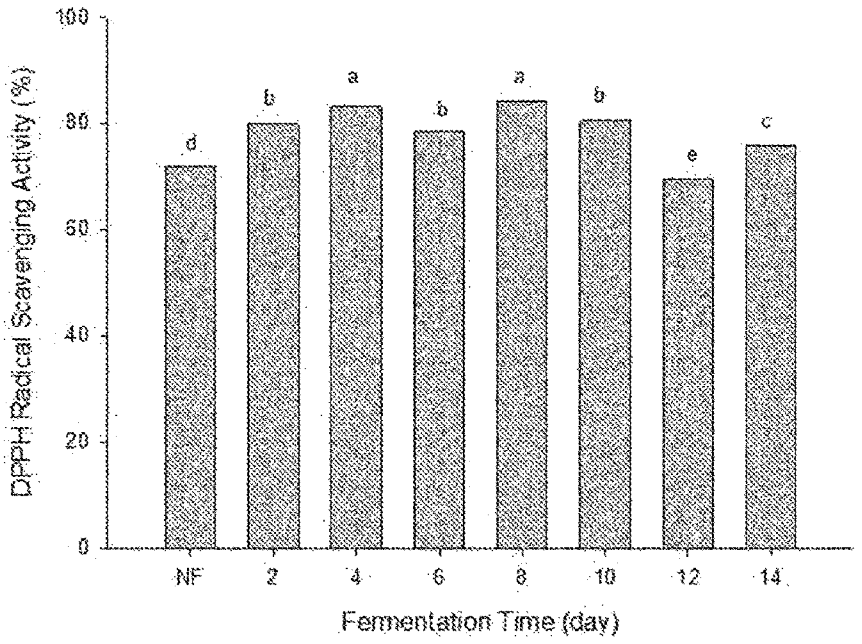
[Fig. 6B]
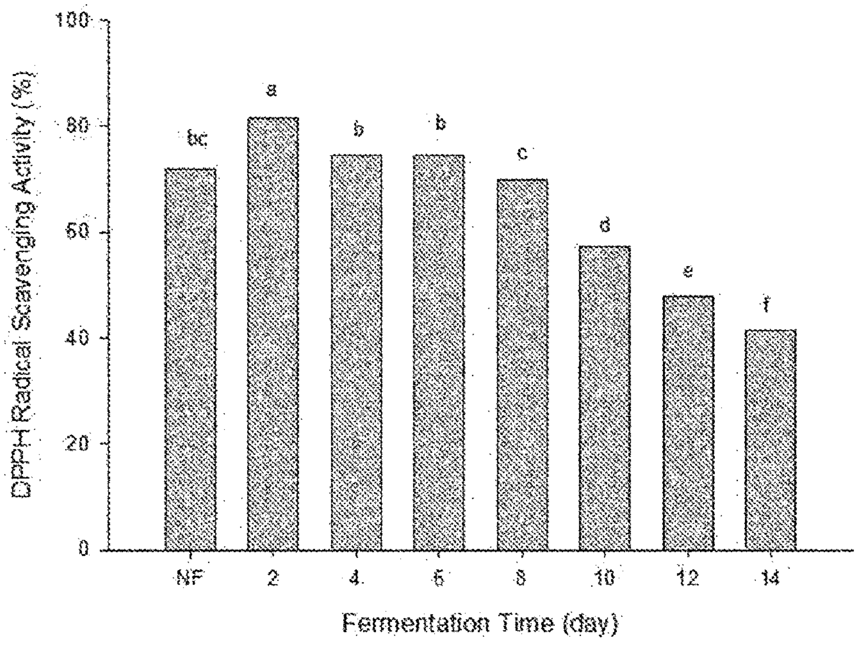

[Fig. 6C]
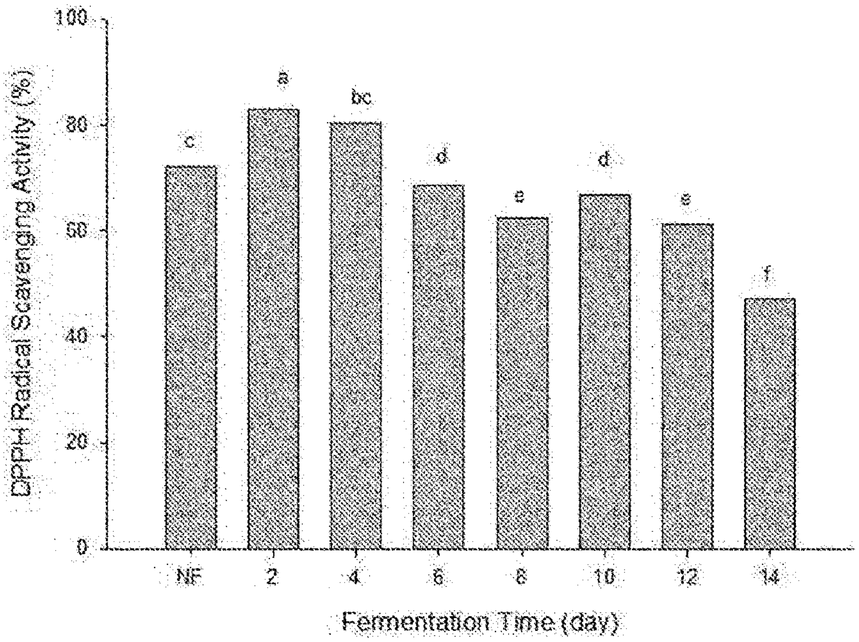
[Fig. 6D]
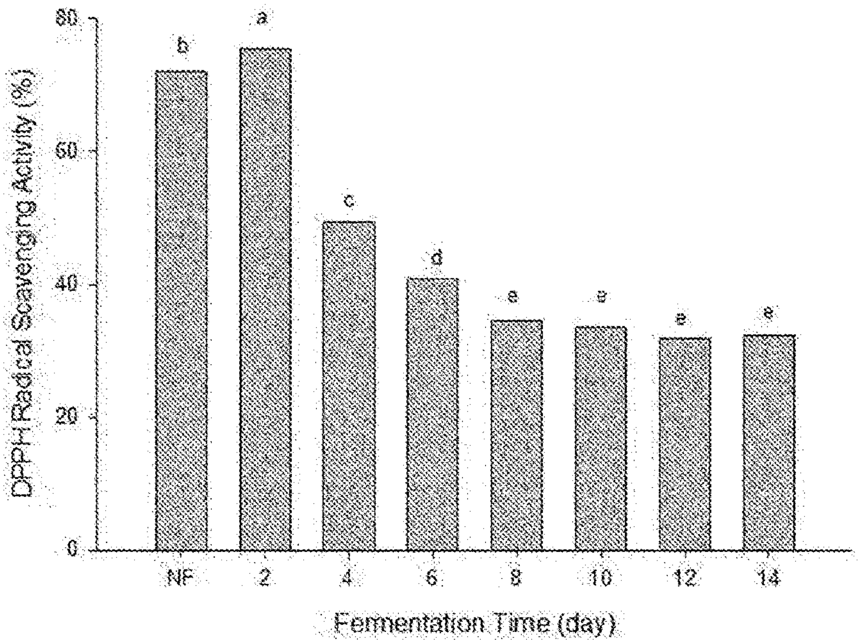

[Fig. 7A]
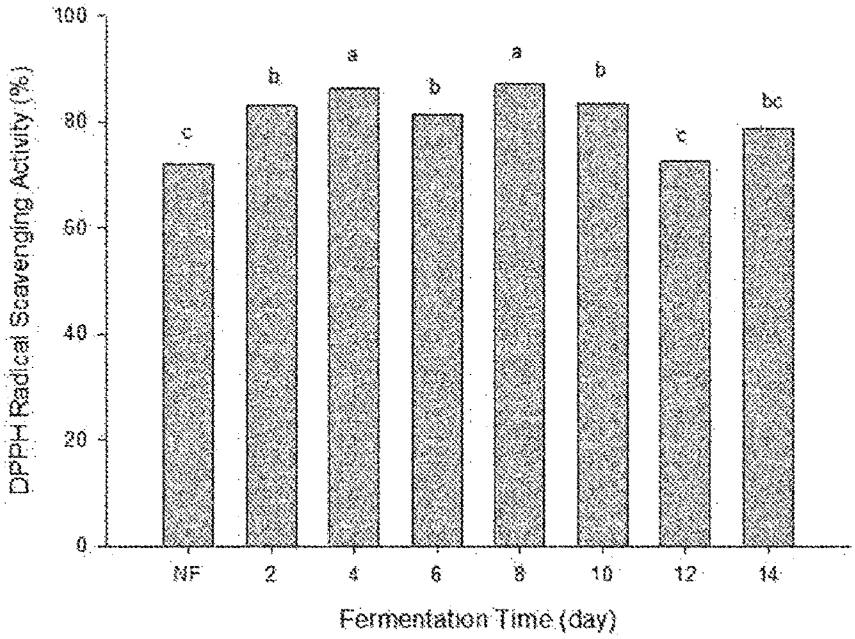
[Fig. 7B]
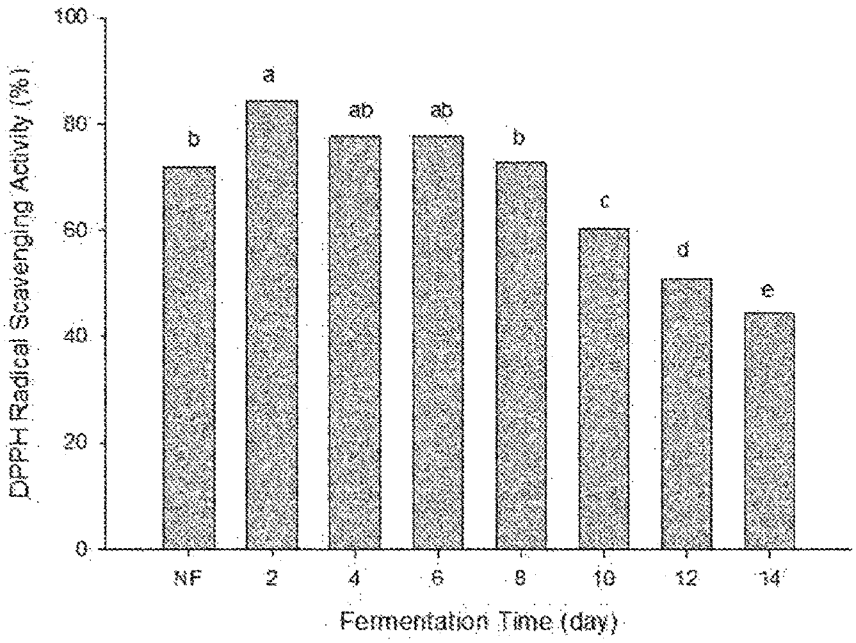

[Fig. 7C]
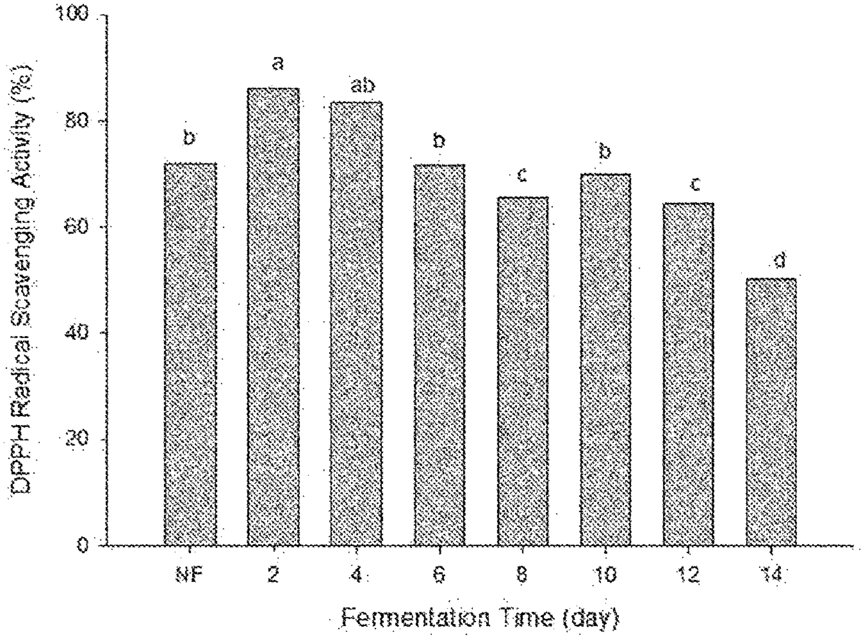
[Fig. 7D]
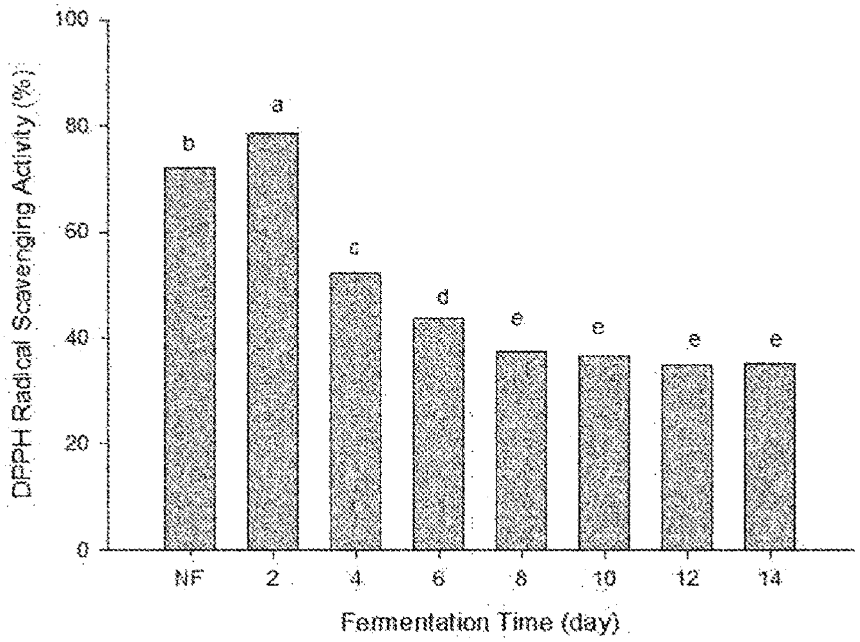

[Fig. 8A]
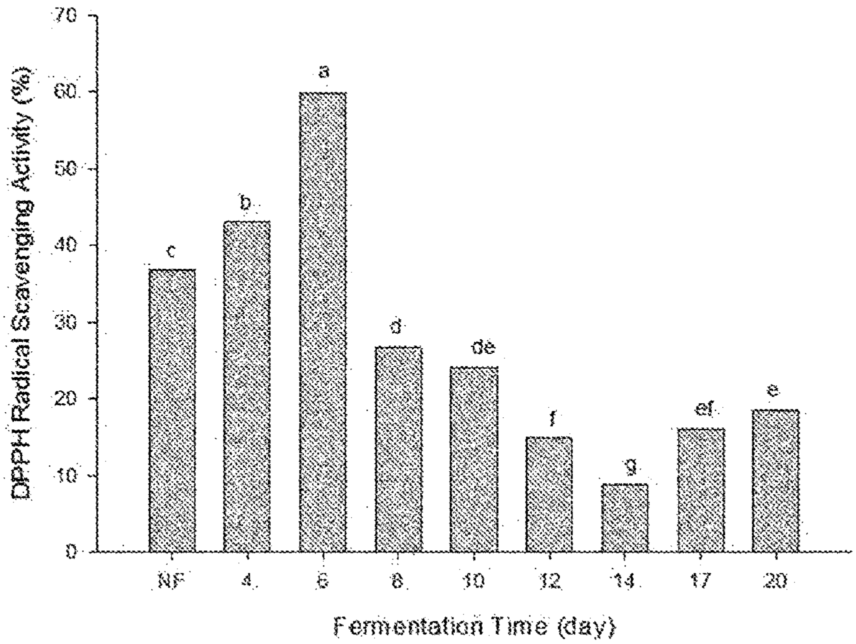
[Fig. 8B]
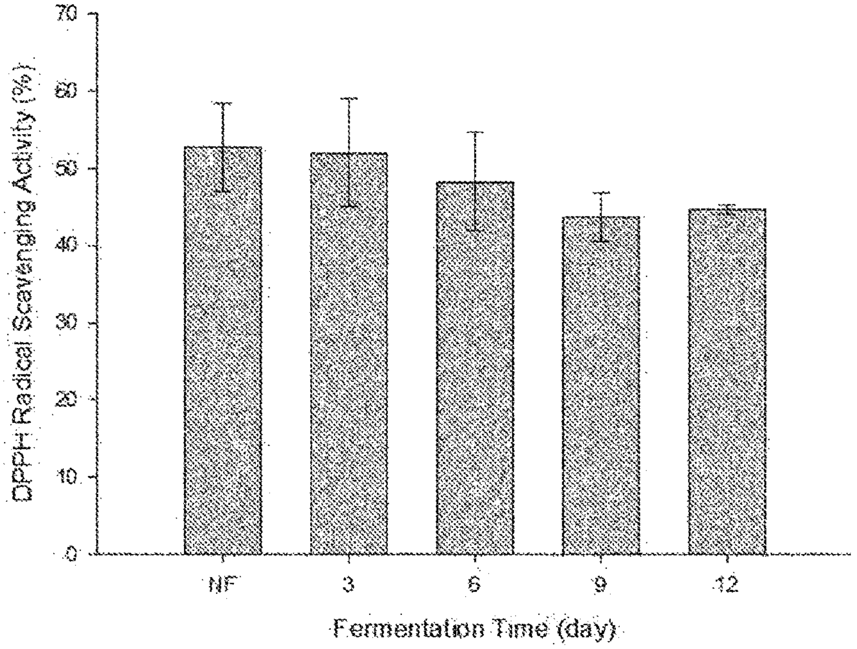

[Fig. 8C]
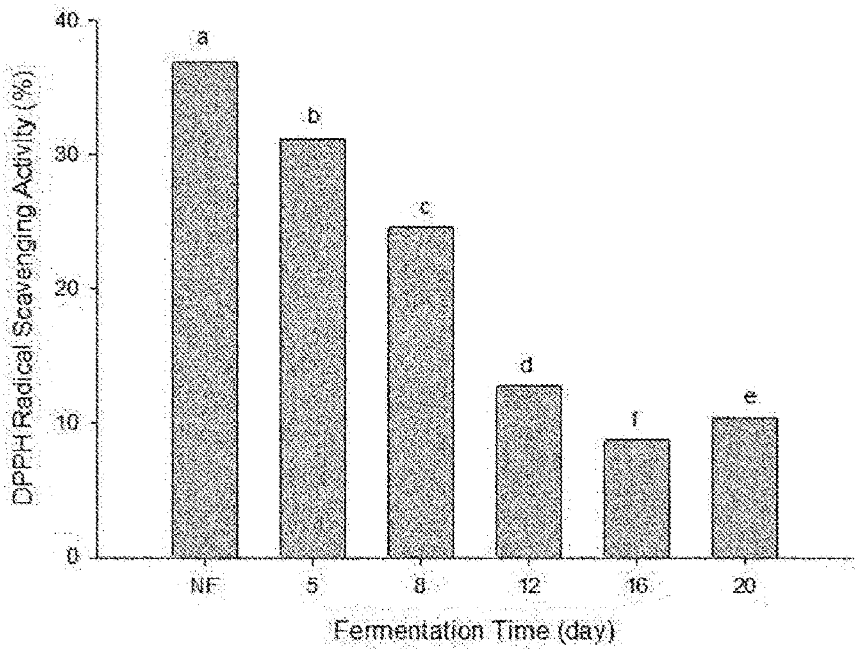
[Fig. 9A]
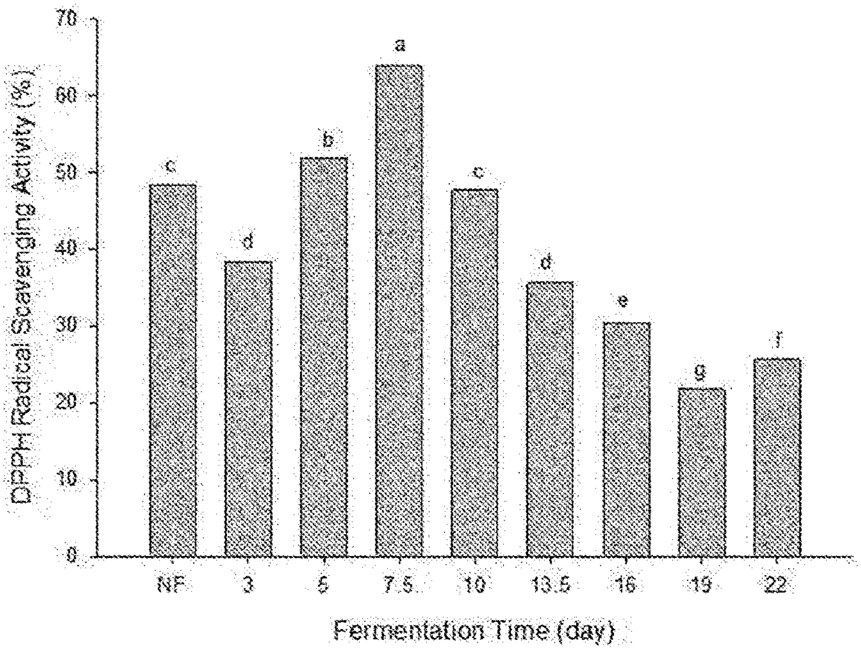

[Fig. 9B]
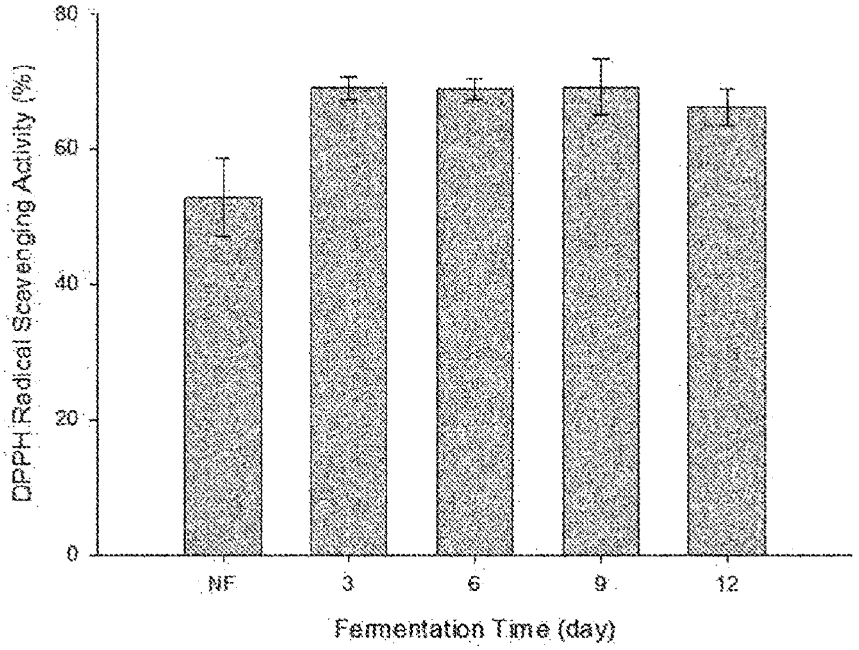
[Fig. 9C]
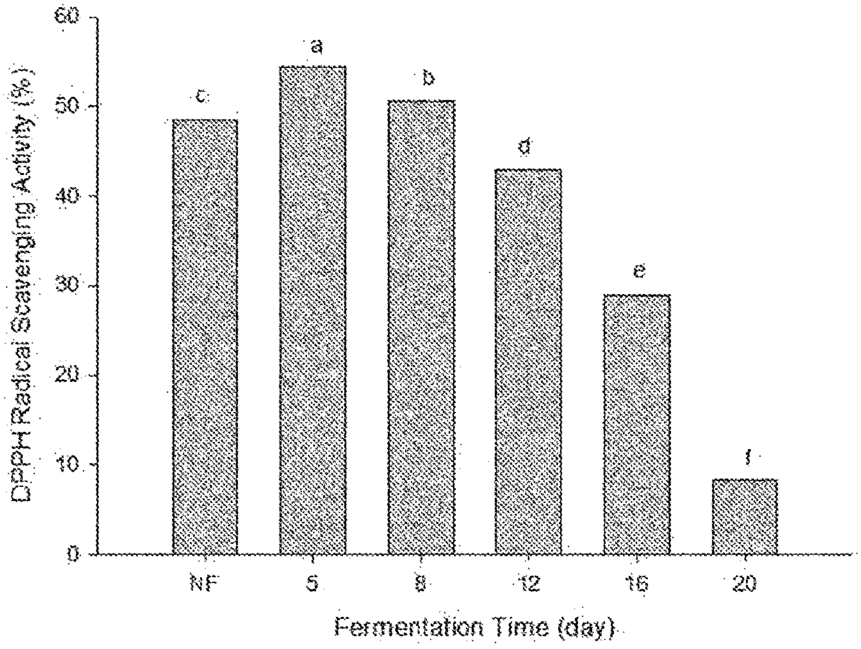

[Fig. 10A]
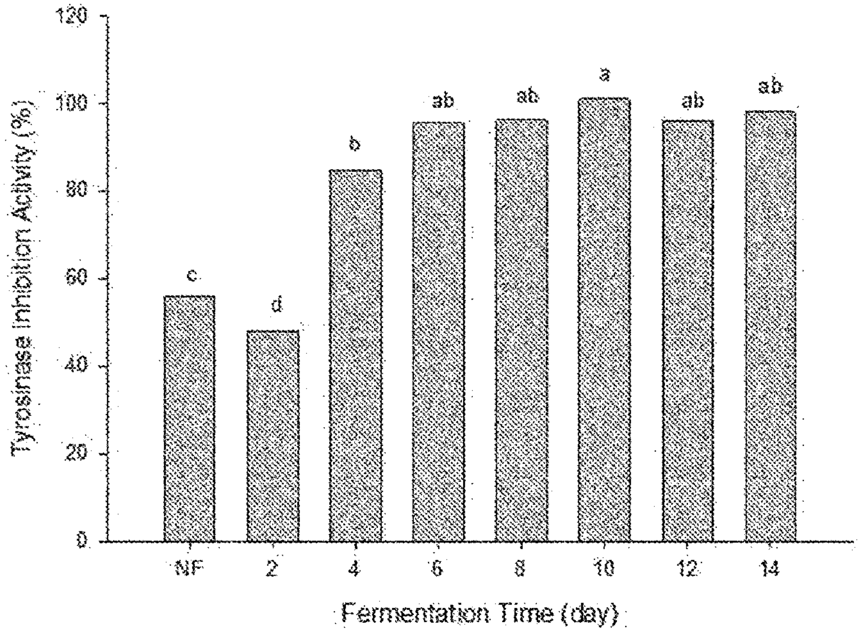
[Fig. 10B]
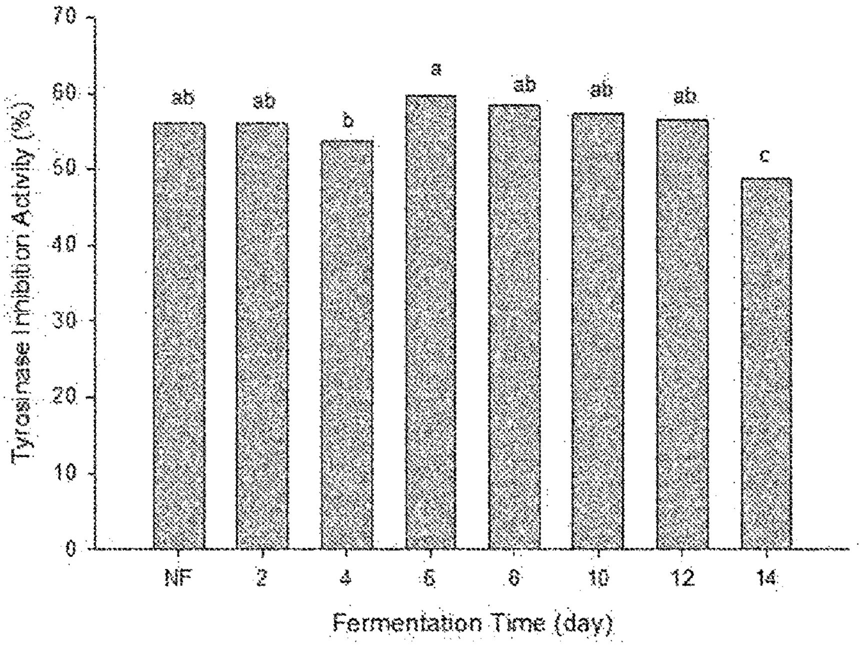

[Fig. 10C]
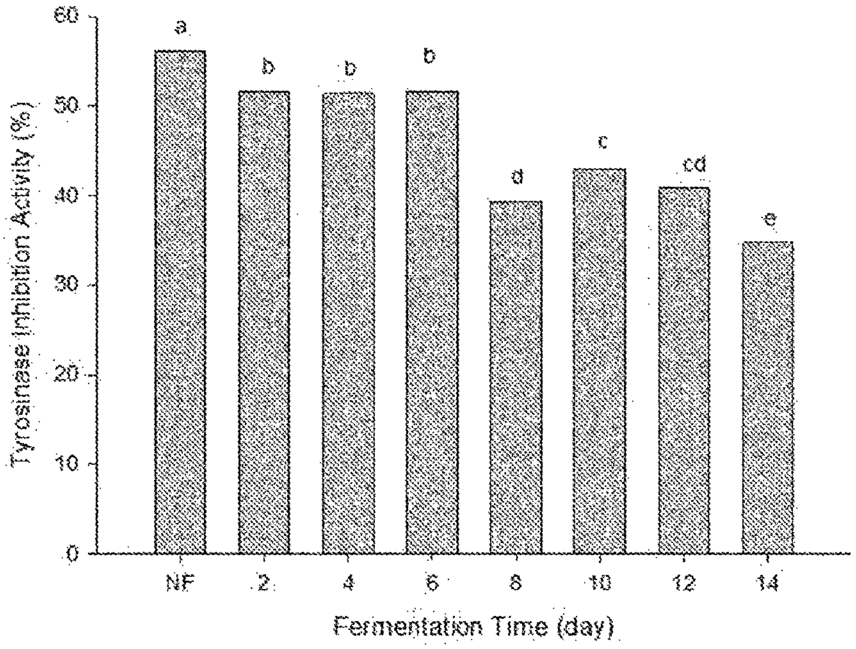
[Fig. 10D]
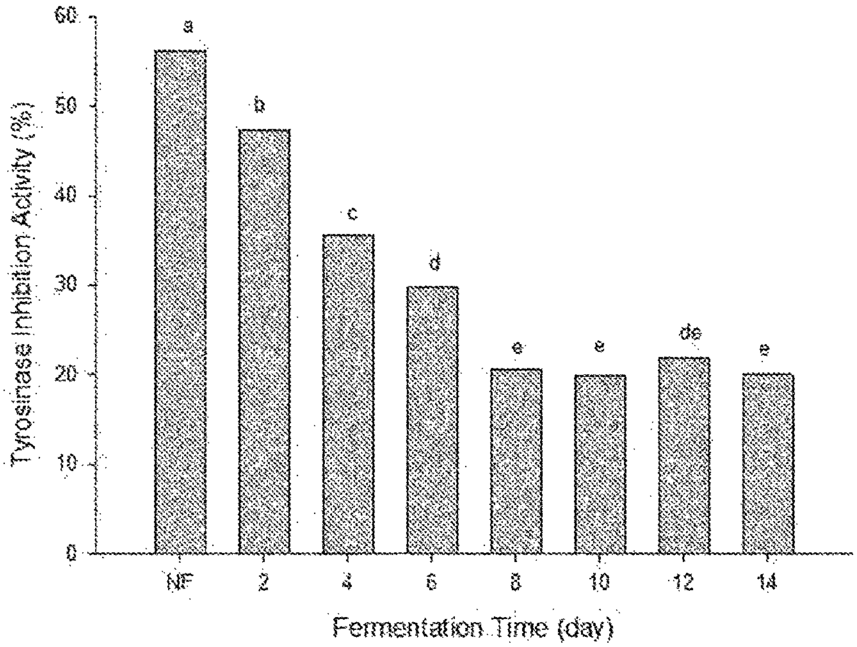

[Fig. 11A]
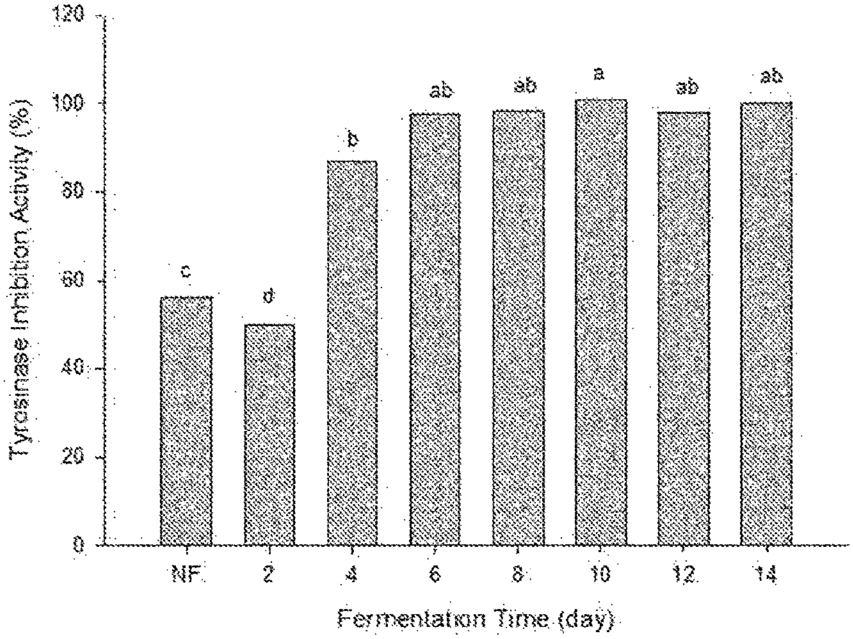
[Fig. 11B]
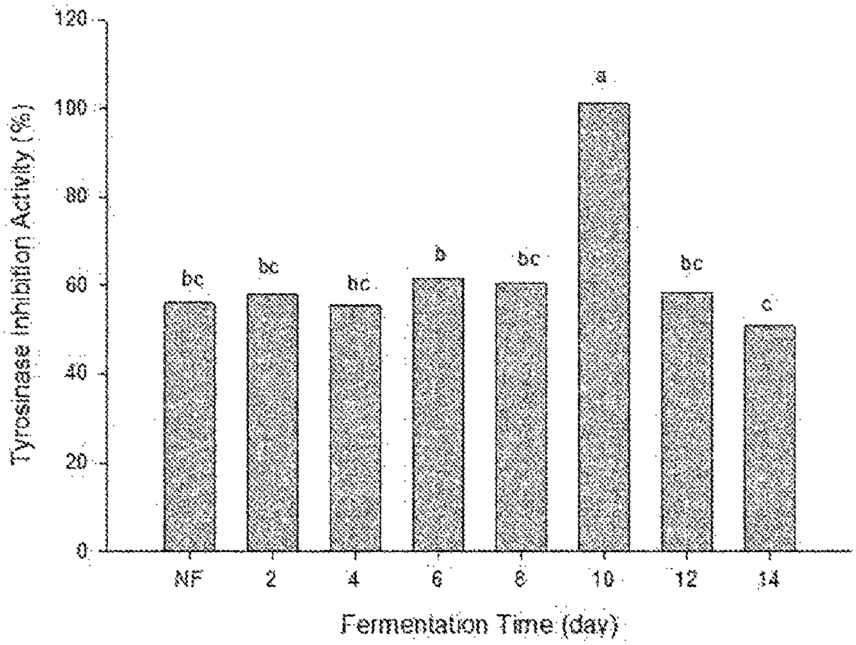

[Fig. 11C]
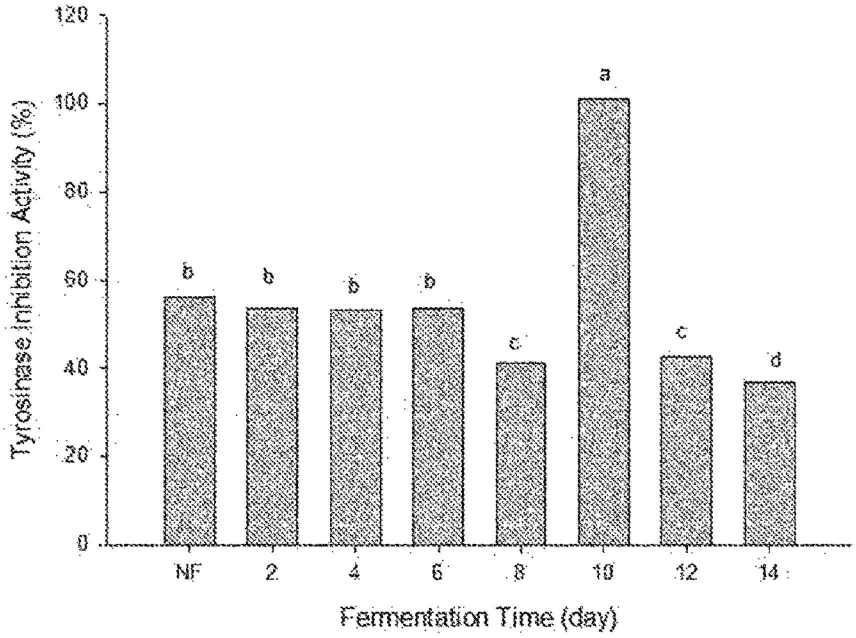
[Fig. 11D]
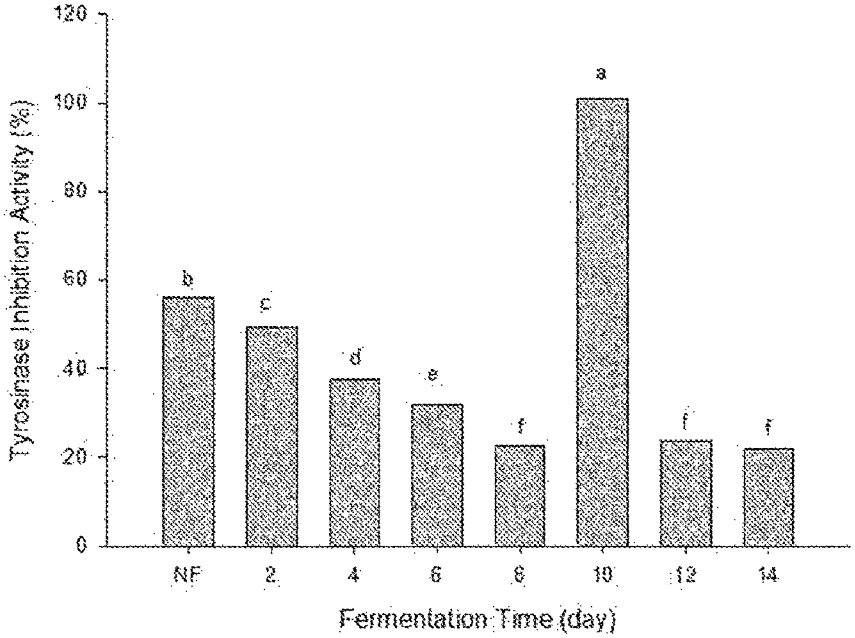

[Fig. 12A]
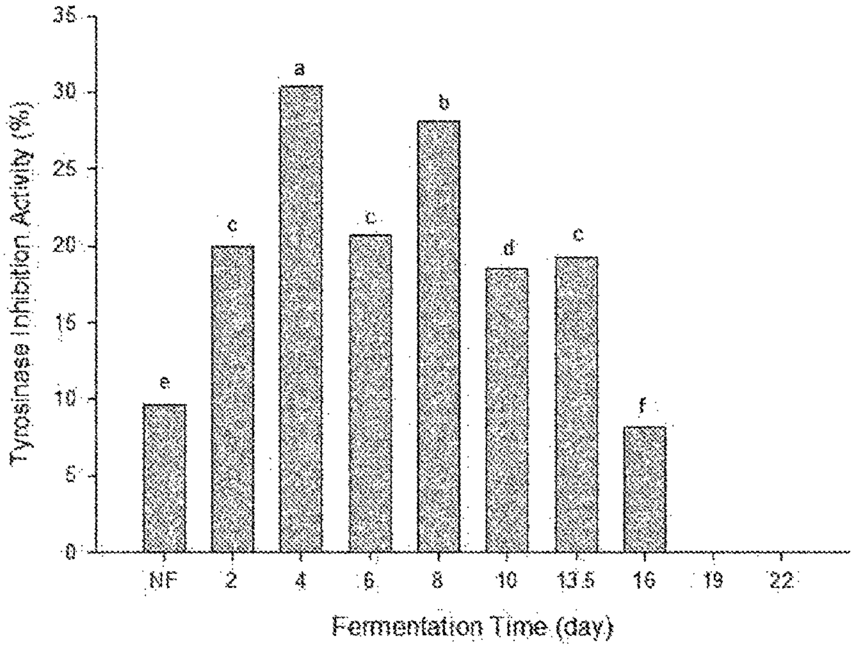
[Fig. 12B]
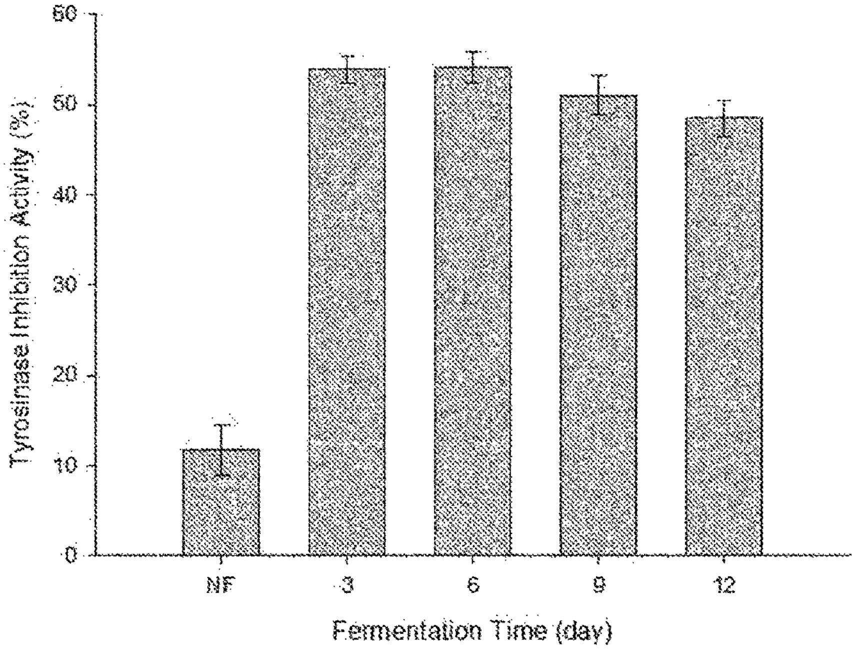

[Fig. 12C]
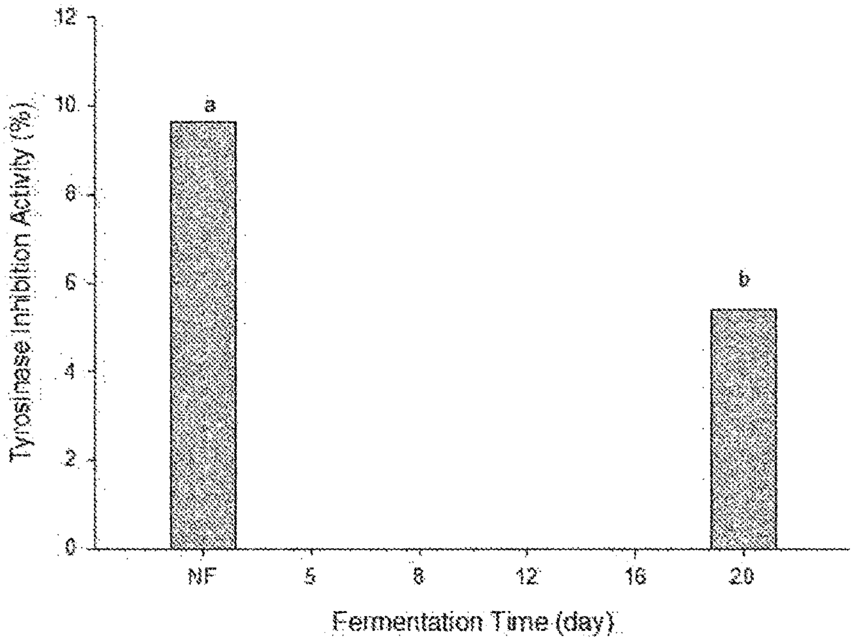
[Fig. 13A]
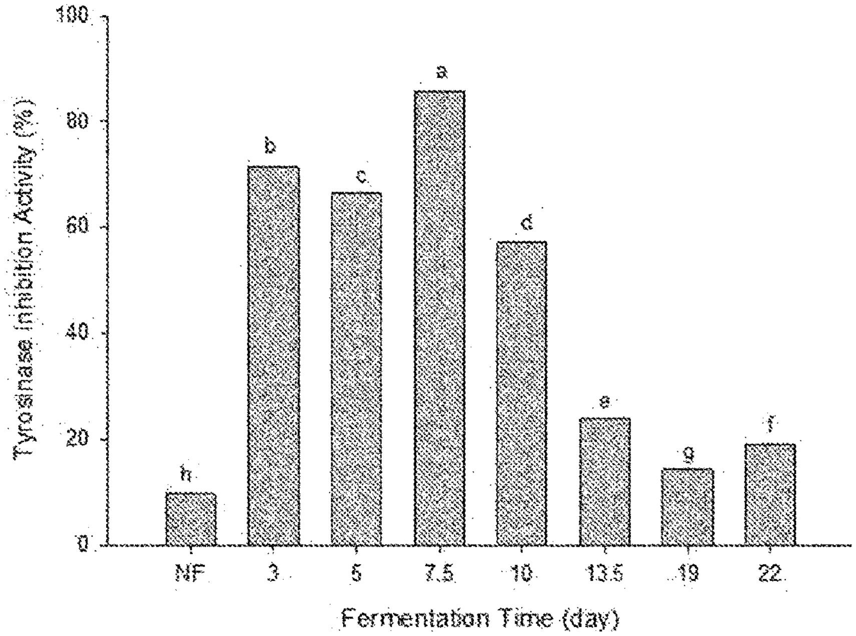

[Fig. 13B]
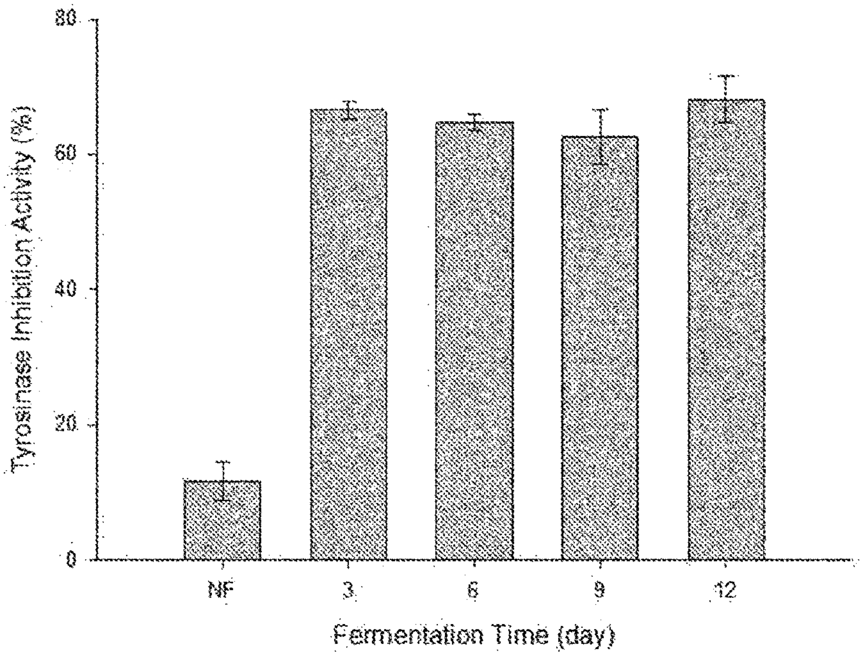
[Fig. 14A]
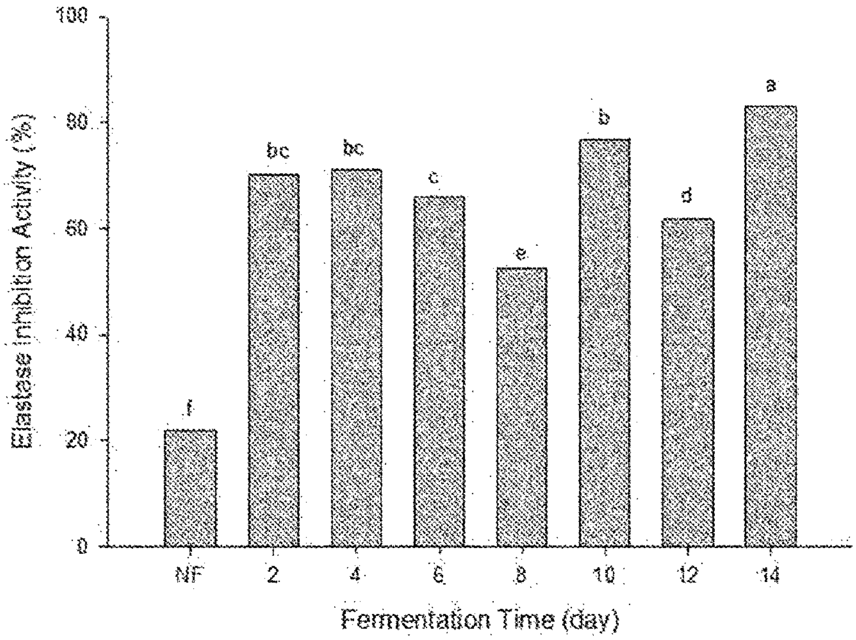

[Fig. 14B]
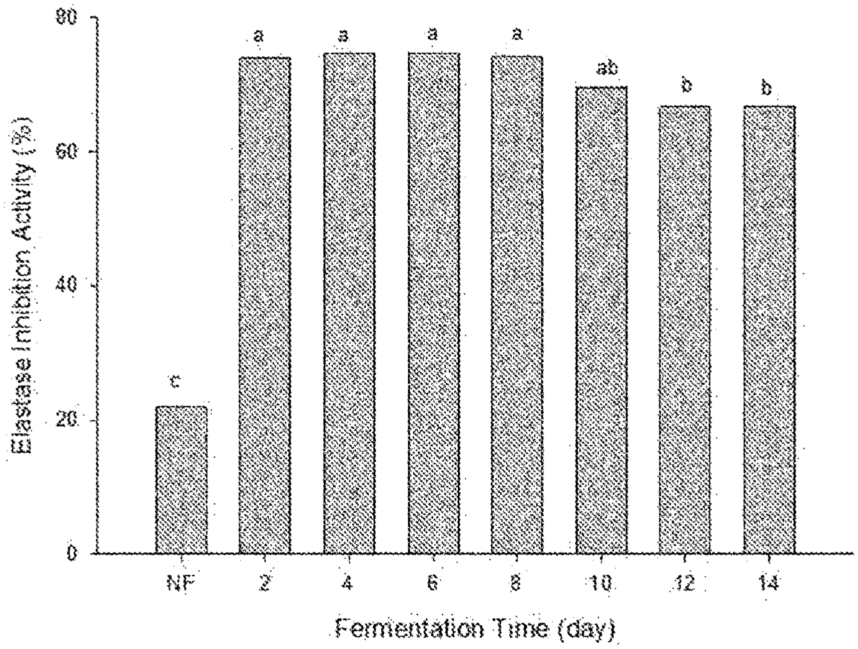
[Fig. 14C]
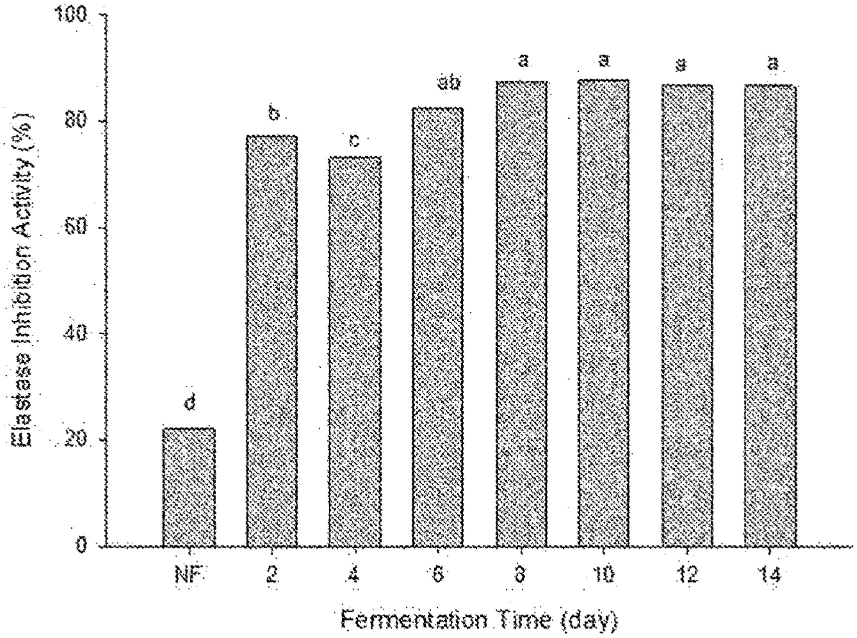

[Fig. 14D]
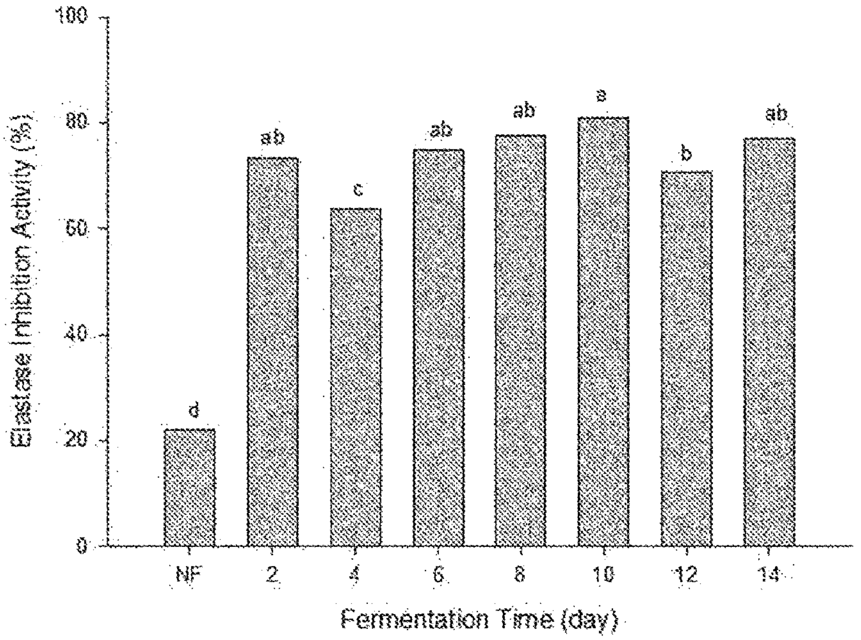
[Fig. 15A]
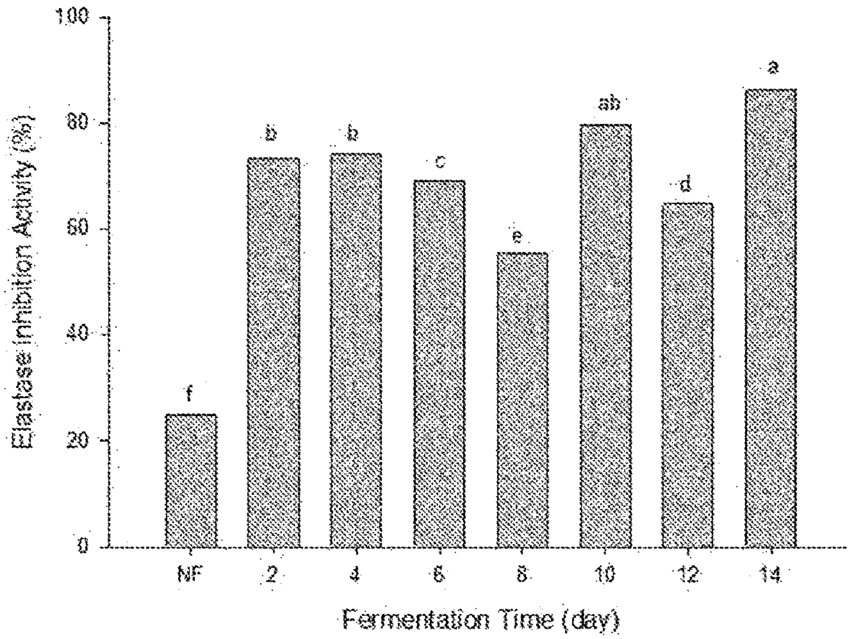

[Fig. 15B]
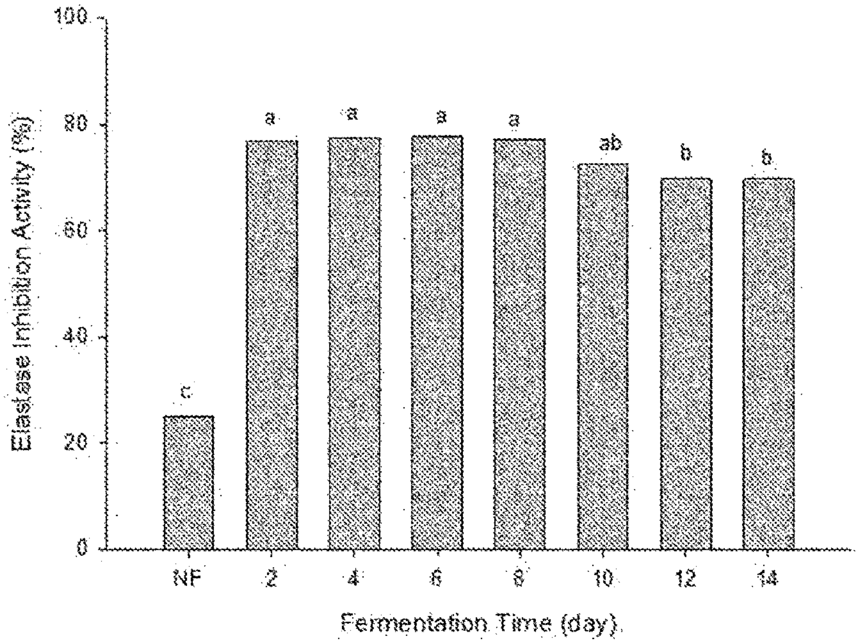
[Fig. 15C]
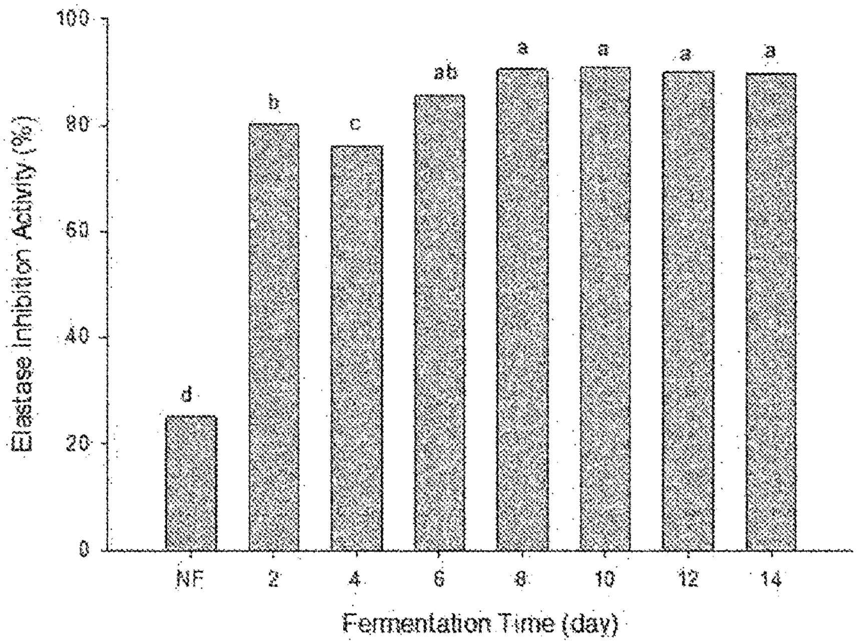

[Fig. 15D]
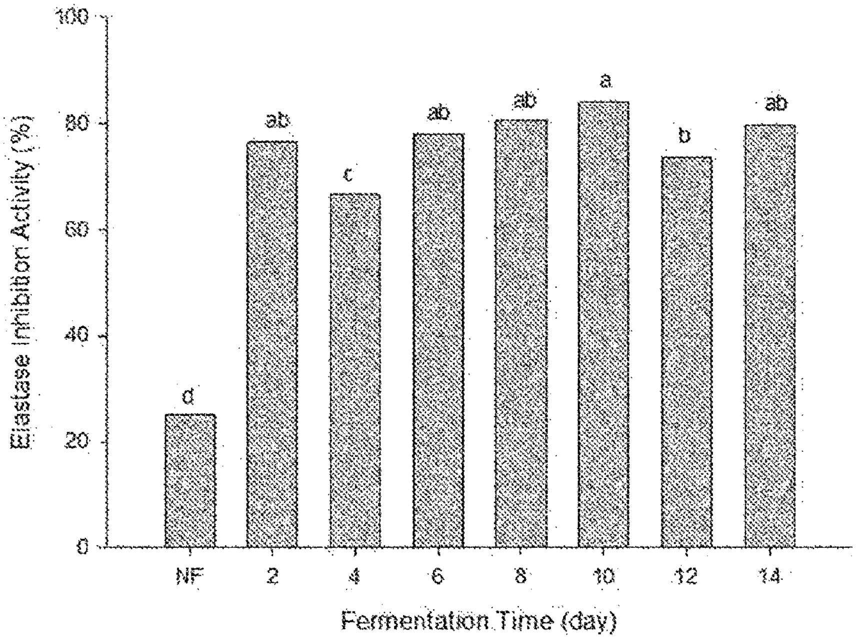
[Fig. 16A]
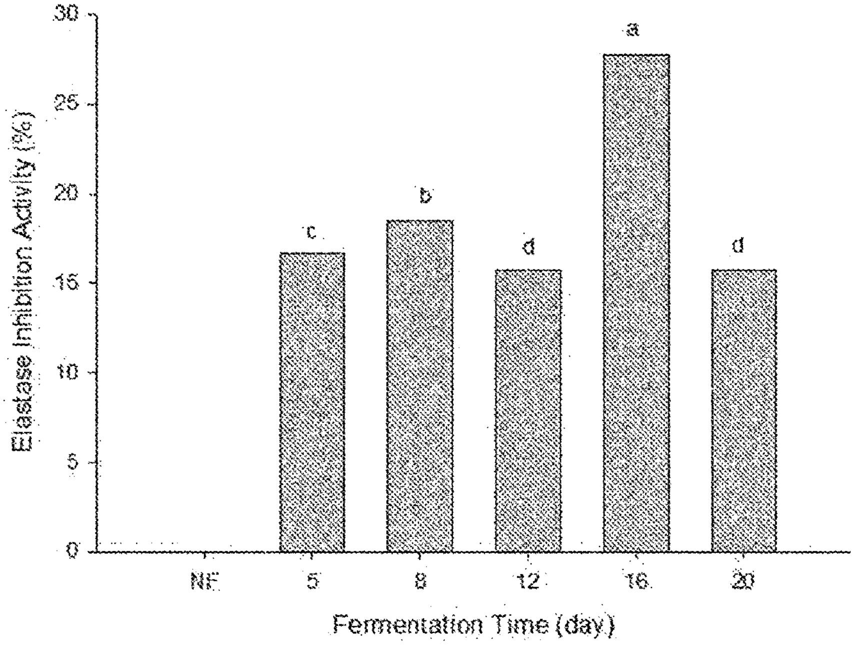

[Fig. 16B]
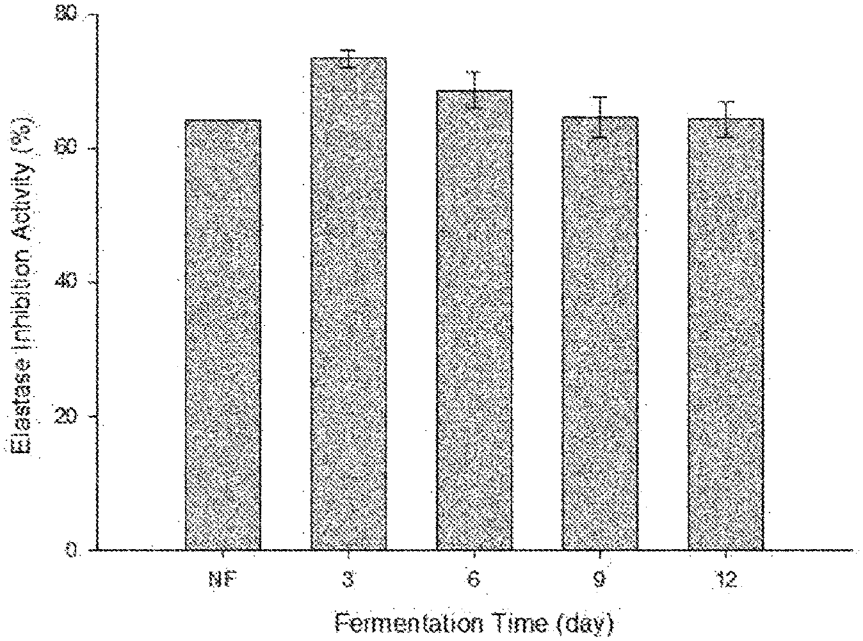
[Fig. 17A]
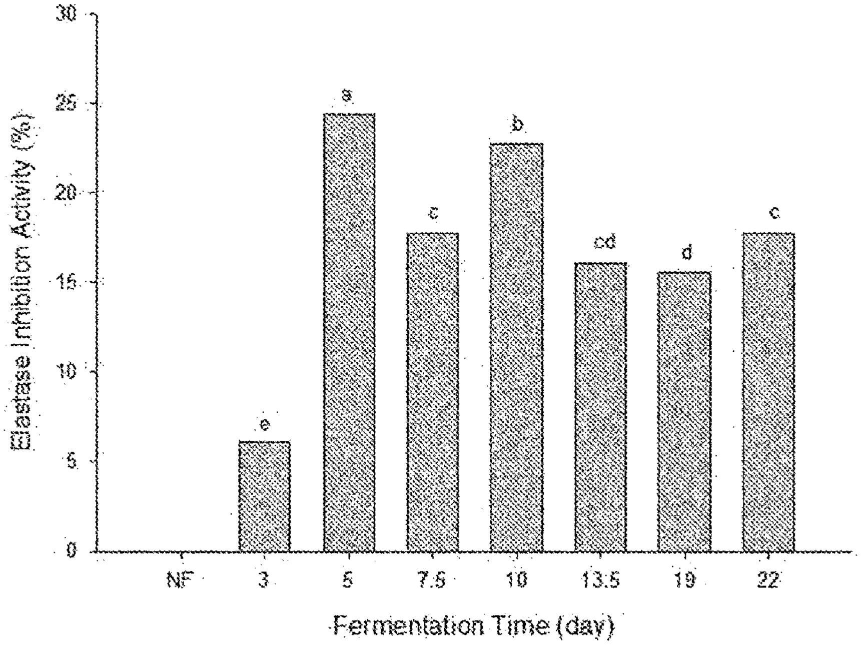

[Fig 17B]
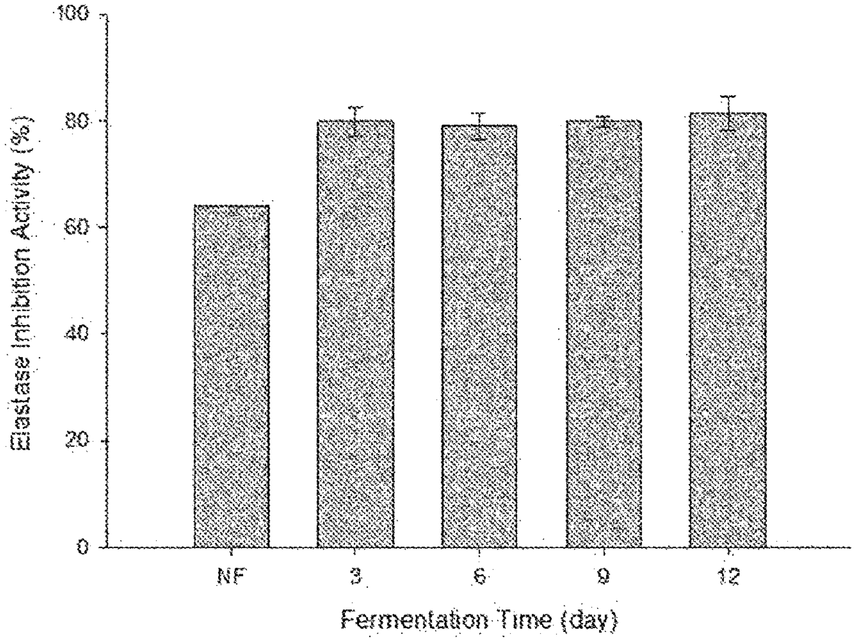
[Fig 17C]
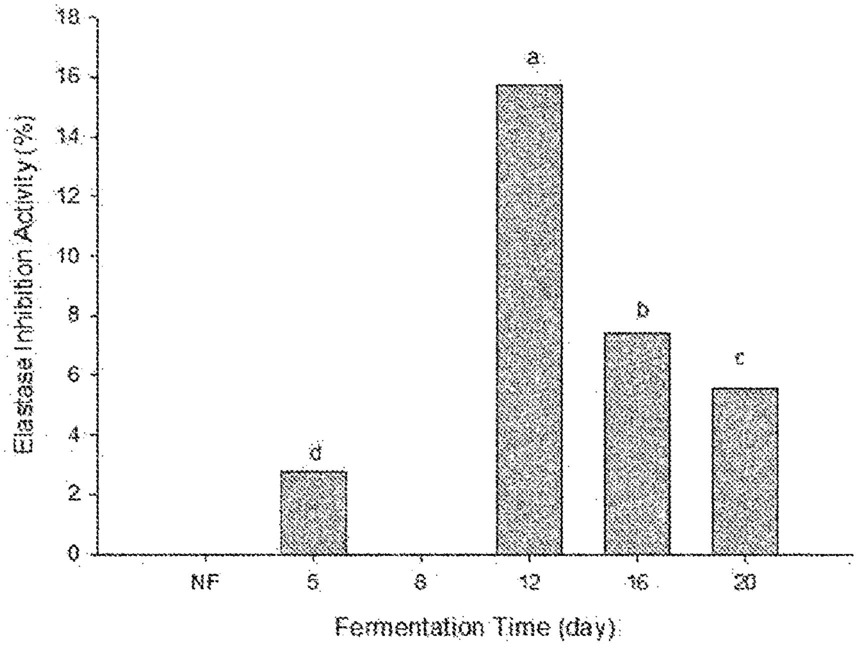

COSMETIC COMPOSITION COMPRISING FERMENTED CHESTNUT HUSK EXTRACT OR FRACTION THEREOF AS ACTIVE INGREDIENT

CROSS REFERENCE TO RELATED APPLICATIONS

This application is a U.S. National Stage Application of International Application No. PCT/KR2021/007239, filed on Jun. 10, 2021, which claims the benefit under 35 USC 119 (a) and 365(b) of Korean Patent Application No. 10-2020-0074885 filed on Jun. 19, 2020 and Korean Patent Application No. 10-2021-0074719 filed on Jun. 9, 2021, in the Korean Intellectual Property Office, the entire disclosures of which are incorporated herein by reference for all purposes.

TECHNICAL FIELD

The present invention relates to a cosmetic composition containing a fermented chestnut inner shell extract or fraction thereof as an active ingredient.

BACKGROUND ART

Skin aging may be broadly classified into aging attributable to internal factors and aging attributable to external factors and structural and functional changes of the skin occur depending on the factors. Since the skin is always exposed to the external environment, changes in the skin due to aging are affected by external factors such as UV rays. As aging progresses, the skin becomes dry, darkens, loses elasticity and wrinkles.

An oxygen free radical, which is the main cause of aging, is inevitably generated in metabolic processes that require oxygen. The oxygen free radical remains very unstable and thus attacks the tissues of the body, and oxidizes and damages cells, causing aging.

The oxygen free radical oxidizes proteins in the body or lipids in cell membranes, and thus causes deterioration in the functions of the human body and damages DNA, which may cause mutations or cancer. In addition, the oxygen free radical attacks collagen and skin fibers that impart elasticity to the skin, thus causing skin aging, skin sagging and wrinkles.

The human body has a defense enzyme system that removes excess oxygen free radicals such as SOD (superoxide dismutase). Until a person's twenties, the human defense system of antioxidant enzymes is active and thus has no difficulty in keeping the body healthy. Then, as the functions of antioxidant enzymes rapidly weaken with age, the human body is more easily exposed to oxygen free radicals and aging is accelerated. Therefore, it is necessary to properly remove oxygen free radicals in order to realize anti-aging effects.

Although there may be differences between the structures of the skin, as histological changes caused by aging, the thickness of the epidermis becomes thinner, the boundary between the epidermis and the dermis becomes flat, and the number of elastic fibers decreases, resulting in wrinkles.

In addition, wrinkle formation of the skin is fundamentally associated with changes in collagen and elastin in the dermal layer due to aging or aging of the skin under the influence of ultraviolet. When collagen and elastin in the skin are reduced, the elasticity of the skin is reduced, thus eventually causing wrinkling.

Melanin functions to protect the human body against cytotoxic substances such as amines, oxygen free radicals, and metal ions, but causes pigmentation such as spots and freckles and promotes skin aging when overproduced.

Melanin is a phenolic polymer that is widely distributed in nature and is a complex of black pigment and protein. The starting material, for the production of melanin, an amino acid called "tyrosine" in melanocytes, is converted into DOPA, which is oxidized again into DOPA-quinone, via the oxidative enzyme tyrosinase. Then, the DOPA-quinone automatically oxidizes to produce black-brown melanin. Therefore, whitening cosmetics may be expected to have a whitening effect by inhibiting melanin production based on the inhibition of the enzymatic activity of tyrosinase.

Meanwhile, chestnut inner shells are the inner shells of chestnuts, which are fruits of Castanea crenata Sieb, a deciduous broad-leaved tree belonging to the Fagaceae family, and are mostly discarded during processing of chestnuts, but are known to contain large amounts of valuable ingredients such as tannic acid, gallic acid, and catechin.

The related art, Korean Patent No. 10-0308178 discloses a cosmetic composition for ameliorating skin wrinkles containing a chestnut inner shell extract, but has a problem in that the wrinkle-ameliorating effect is unsatisfactory.

Accordingly, while researching the efficacy of chestnut inner shells, the present inventors found that antioxidant, skin-whitening and wrinkle-ameliorating effects were greatly improved using an extract obtained by fermenting and extracting chestnut inner shells or a fraction thereof and completed the present invention.

DISCLOSURE

Technical Problem

It is an object of the present invention to provide a cosmetic composition containing a fermented chestnut inner shell extract or fraction thereof as an active ingredient.

Technical Solution

In accordance with one aspect of the present invention, the above and other objects can be accomplished by the provision of a cosmetic composition containing a fermented chestnut inner shell extract or fraction thereof as an active ingredient.

According to the present invention, the fermented chestnut inner shell extract may be obtained by inoculation with one or more fungi selected from the group consisting of *Aspergillus* spp. strains and *Monascus* spp. strains, followed by fermentation and extraction.

In this case, the *Aspergillus* spp. strains may be at least one selected from the group consisting of *A. sojae, A. brasiliensis, A. awamori* and *A. oryzae.*

In addition, the *Monascus* spp. strains may be at least one selected from the group consisting of *M. Pilosus, M. Kaoliang* and *M. Purpureus.*

Also, the fermentation may be solid fermentation, liquid fermentation, or a combination thereof.

Also, the fermentation may be performed for 2 to 20 days.

Also, the fermentation may be performed by inoculating 0.1 to 20 parts by weight of the fungus with respect to 100 parts by weight of the chestnut inner shell and then culturing the chestnut inner shell at 20 to 45° C.

According to the present invention, the fermented chestnut inner shell extract may be obtained by extraction using at least one extraction solvent selected from the group consisting of water, C1-C4 anhydrous or hydrous alcohol, ethyl acetate, acetone, glycerin, ethylene glycol, propylene glycol and butylene glycol.

According to the present invention, the fraction may be obtained by fractionating the fermented chestnut inner shell extract with a solvent selected from the group consisting of hexane, chloroform, ethyl acetate, butanol, water, and a mixture thereof.

According to the present invention, the cosmetic composition may be for antioxidant, skin-whitening and wrinkle-amelioration applications.

According to the present invention, the composition may have a formulation selected from the group consisting of a solution, external ointment, cream, foam, nourishing lotion, softening lotion, pack, softening water, serum, makeup base, essence, soap, liquid detergent, bath agent, sunscreen cream, sun oil, suspension, paste, gel, lotion, powder, soap, surfactant-containing cleanser, oil, powder foundation, emulsion foundation, wax foundation, patch and spray.

Advantageous Effects

The present invention is capable of providing a cosmetic composition that is highly effective in increasing the total phenolic content and improving antioxidant, skin-whitening, and wrinkle-ameliorating activities through fermentation, extraction and fractionation.

DESCRIPTION OF DRAWINGS

FIGS. 1A and 1B show growth curves as a function of fermentation temperature and time conditions of *Aspergillus* spp. strains (FIG. 1A) and *Monascus* spp. strains (FIG. 1B).

FIGS. 2A to 2D show the total phenolic content of the chestnut inner shell extract obtained by solid-fermenting the *Aspergillus* spp. strains (FIG. 2A: *A. sojae*, FIG. 2B: *A. brasiliensis*, FIG. 2C: *A. awamori*, and FIG. 2D: *A. oryzae*, and NF represents a non-fermented chestnut inner shell).

FIGS. 3A to 3D show the total phenolic content of the chestnut inner shell extract obtained by liquid-fermenting the *Aspergillus* spp. strains (FIG. 3A: *A. sojae*, FIG. 3B: *A. brasiliensis*, FIG. 3C: *A. awamori*, and FIG. 3D: *A. oryzae*, and NF represents a non-fermented chestnut inner shell).

FIGS. 4A to 4C show the total phenolic content of the chestnut inner shell extract obtained by solid-fermenting the *Monascus* spp. strains (FIG. 4A: *M. Pilosus*, FIG. 4B: *M. Kaoliang*, and FIG. 4C: *M. Purpureus*, and NF represents a non-fermented chestnut inner shell).

FIGS. 5A to 5C show the total phenolic content of the chestnut inner shell extract obtained by liquid-fermenting the *Monascus* spp. strains (FIG. 5A: *M. Pilosus*, FIG. 5B: *M. Kaoliang*, and FIG. 5C: *M. Purpureus*, and NF represents a non-fermented chestnut inner shell).

FIGS. 6A to 6D show the DPPH radical scavenging activity of the chestnut inner shell extract obtained by solid-fermenting the *Aspergillus* spp. strains (FIG. 6A: *A. sojae*, FIG. 6B: *A. brasiliensis*, FIG. 6C: *A. awamori*, and FIG. 6D: *A. oryzae*, and NF represents a non-fermented chestnut inner shell).

FIGS. 7A to 7D show the DPPH radical scavenging activity of the chestnut inner shell extract obtained by liquid-fermenting the *Aspergillus* spp. strains (FIG. 7A: *A. sojae*, FIG. 7B: *A. brasiliensis*, FIG. 7C: *A. awamori*, and FIG. 7D: *A. oryzae*, and NF represents a non-fermented chestnut inner shell).

FIGS. 8A to 8C show the total phenolic content of the chestnut inner shell extract obtained by solid-fermenting the *Monascus* spp. strains (FIG. 8A: *M. Pilosus*, FIG. 8B: *M. Kaoliang*, and FIG. 8C: *M. Purpureus*, and NF represents a non-fermented chestnut inner shell).

FIGS. 9A to 9C show the total phenolic content of the chestnut inner shell extract obtained by liquid-fermenting the *Monascus* spp. strains (FIG. 9A: *M. Pilosus*, FIG. 9B: *M. Kaoliang*, and FIG. 9C: *M. Purpureus*, and NF represents a non-fermented chestnut inner shell).

FIGS. 10A to 10D show the tyrosinase inhibitory activity of the chestnut inner shell extract obtained by solid-fermenting the *Aspergillus* spp. strains (FIG. 10A: *A. sojae*, FIG. 10B: *A. brasiliensis*, FIG. 10C: *A. awamori*, and FIG. 10D: *A. oryzae*, and NF represents a non-fermented chestnut inner shell).

FIGS. 11A to 11D show the tyrosinase inhibitory activity of the chestnut inner shell extract obtained by liquid-fermenting the *Aspergillus* spp. strains (FIG. 11A: *A. sojae*, FIG. 11B: *A. brasiliensis*, FIG. 11C: *A. awamori*, and FIG. 11D: *A. oryzae*, and NF represents a non-fermented chestnut inner shell).

FIGS. 12A to 12C show the tyrosinase inhibitory activity of the chestnut inner shell extract obtained by solid-fermenting the *Monascus* spp. strains (FIG. 12A: *M. Pilosus*, FIG. 12B: *M. Kaoliang*, and FIG. 12C: *M. Purpureus*, and NF represents a non-fermented chestnut inner shell).

FIGS. 13A and 13B show the tyrosinase inhibitory activity of the chestnut inner shell extract obtained by liquid-fermenting the *Monascus* spp. strains (FIG. 13A: *M. Pilosus*, FIG. 13B: *M. Kaoliang*, and NF represents a non-fermented chestnut inner shell).

FIGS. 14A to 14D show the elastase inhibitory activity of the chestnut inner shell extract obtained by solid-fermenting the *Aspergillus* spp. strains (FIG. 14A: *A. sojae*, FIG. 14B: *A. brasiliensis*, FIG. 14C: *A. awamori*, and FIG. 14D: *A. oryzae*, and NF represents a non-fermented chestnut inner shell).

FIGS. 15A to 15D show the elastase inhibitory activity of the chestnut inner shell extract obtained by liquid-fermenting the *Aspergillus* spp. strains (FIG. 15A: *A. sojae*, FIG. 15B: *A. brasiliensis*, FIG. 15C: *A. awamori*, and FIG. 15D: *A. oryzae*, and NF represents a non-fermented chestnut inner shell).

FIGS. 16A and 16B show the elastase inhibitory activity of the chestnut inner shell extract obtained by solid-fermenting the *Monascus* spp. strains (FIG. 16A: *M. Pilosus*, FIG. 16B: *M. Kaoliang*, and NF represents a non-fermented chestnut inner shell).

FIGS. 17A to 17C show the elastase inhibitory activity of the chestnut inner shell extract obtained by liquid-fermenting the *Monascus* spp. strains (FIG. 17A: *M. Pilosus*, FIG. 17B: *M. Kaoliang*, and FIG. 17C: *M. Purpureus*, and NF represents a non-fermented chestnut inner shell).

BEST MODE

Unless defined otherwise, all technical and scientific terms used herein have the same meanings as appreciated by those skilled in the field to which the present invention pertains. In general, the nomenclature used herein is well-known in the art and is ordinarily used.

The present invention provides a cosmetic composition containing a fermented chestnut inner shell extract or fraction thereof as active ingredient.

The fermented chestnut inner shell extract may be obtained by inoculation with one or more fungi selected from the group consisting of *Aspergillus* spp. strains and *Monascus* spp. strains, followed by fermentation and extraction. In particular, as can be seen from the results of Example given below, it is preferable to use, as the *Aspergillus* sp. strain, at least one selected from the group consisting of *A. sojae, A. brasiliensis, A. awamori* and *A. oryzae* and it is preferable to use, as the *Monascus* spp. strain, at least one selected from the group consisting of *M. Pilosus, M. Kaoliang* and *M. Purpureus*. When fermentation is performed using these strains, the total phenolic content, DPPH radical scavenging activity (DPPH), antioxidant activity, tyrosinase inhibitory activity, elastase inhibitory activity, and the like of the fermented chestnut inner shell extract can be greatly improved.

Also, the fermentation may be carried out by solid fermentation, liquid fermentation, or a combination thereof. The fermentation is preferably performed for 2 to 20 days. As can be seen from Example given below, when the fermentation period is shorter than the period defined above, the effects of improving the total phenolic content, DPPH radical scavenging activity, antioxidant activity, tyrosinase inhibitory activity, elastase inhibitory activity, and the like of the fermented chestnut inner shell extract are insufficient and when the fermentation period is longer than the period defined above, there is a problem that the above-described effects are no longer improved.

Also, the fermentation may be performed by inoculating 0.1 to 20 parts by weight of the fungus with respect to 100 parts by weight of the chestnut inner shell and then culturing the chestnut inner shell at 20 to 45° C.

Also, the fermented chestnut inner shell extract may be obtained by extraction using at least one extraction solvent selected from the group consisting of water, C1-C4 anhydrous or hydrous alcohol, ethyl acetate, acetone, glycerin, ethylene glycol, propylene glycol and butylene glycol, more preferably, a solvent selected from water, C1-C4 anhydrous alcohol or hydrous alcohol, and a mixture thereof. In this case, the C1-C4 alcohol includes methanol, ethanol, n-propanol, iso-propanol, n-butanol, tert-butanol, or the like. Among the extraction solvents, most preferred is hydrous ethanol or methanol. The amount of ethanol or methanol that is contained is preferably 30 to 90% by volume, more preferably 40 to 70% by volume.

Also, the fraction refers to a product obtained by performing fractionation in order to separate a specific component or a specific component group from a mixture containing various components, and a fractionation method for obtaining the fraction is not particularly limited and may be any of ordinary methods used in the art. As a non-limiting example of the fractionation method, the fraction may be obtained from the extract by treating the extract obtaining by extracting the fermented chestnut inner shell with a predetermined solvent.

In the present invention, the type of the fractionation solvent used to obtain the fraction is not particularly limited and any solvent known in the art may be used. Non-limiting examples of the fractionation solvent include polar solvents such as water, and alcohols including ethanol and butanol, and non-polar solvents such as hexane, ethyl acetate, and chloroform. These solvents may be used alone or in combination of two or more thereof.

Also, the fermented chestnut inner shell extract in the composition of the present invention may be present in a powder or liquid form in an amount of 0.01 to 40% by weight based on the total weight of the cosmetic composition, and preferably in a powder or liquid form in an amount of 0.1 to 10% by weight based on the total weight of the cosmetic composition.

Also, as can be seen from the results of Example given below, the cosmetic composition of the present invention may be for antioxidant, skin-whitening and wrinkle-amelioration applications.

The cosmetic composition of the present invention may be prepared as a formulation selected from the group consisting of a solution, external ointment, cream, foam, nourishing lotion, softening lotion, pack, softening water, emulsion, makeup base, essence, soap, liquid detergent, bath agent, sunscreen cream, sun oil, suspension, emulsion, paste, gel, lotion, powder, soap, surfactant-containing cleanser, oil, powder foundation, emulsion foundation, wax foundation, patch and spray, but is not limited thereto.

The cosmetic composition of the present invention may further include at least one cosmetically acceptable carrier incorporated in common skin cosmetics, and common ingredients incorporated in skin cosmetics include, for example, an oil, water, surfactant, humectant, lower alcohol, a thickener, a chelating agent, a colorant, a preservative, a fragrance, and the like, but is not limited thereto.

The cosmetically acceptable carrier incorporated in the cosmetic composition of the present invention varies depending on the formulation of the cosmetic composition.

When the formulation of the present invention is an ointment, paste, cream or gel, the carrier may be an animal oil, vegetable oil, wax, paraffin, starch, tragacanth, cellulose derivative, polyethylene glycol, silicone, bentonite, silica, talc, zinc oxide, or the like, but is not limited thereto. These may be used alone or in combination of two or more thereof.

When the formulation of the present invention is a powder or a spray, the carrier may be lactose, talc, silica, aluminum hydroxide, calcium silicate, polyamide powder, or the like. In particular, when the formulation is a spray, additional propellants such as, but not limited to, chlorofluorohydrocarbon, propane/butane or dimethyl ether may be used. These may be used alone or in combination of two or more thereof.

When the formulation of the present invention is a solution or emulsion, the carrier may be a solvent, solubilizer or emulsifier, for example, water, ethanol, isopropanol, ethyl carbonate, ethyl acetate, benzyl alcohol, benzyl benzoate, propylene glycol, 1,3-butyl glycol oil, or the like, and in particular, cottonseed oil, peanut oil, corn germ oil, olive oil, castor oil, sesame oil, glycerol aliphatic ester, or fatty acid ester of polyethylene glycol or sorbitan, but is not limited thereto. These may be used alone or in combination of two or more thereof.

When the formulation of the present invention is a suspension, the carrier may be a liquid diluent such as water, ethanol or propylene glycol, a suspending agent such as ethoxylated isostearyl alcohol, polyoxyethylene sorbitol ester or polyoxyethylene sorbitan ester, crystalline cellulose, aluminum metahydroxide, bentonite, agar or tragacanth, but is not limited thereto. These may be used alone or in combination of two or more thereof.

When the formulation of the present invention is a soap, the carrier may be an alkali metal salt of fatty acid, a hemiester salt of fatty acid, protein hydrolysate of fatty acid, isethionate, lanolin derivative, aliphatic alcohol, vegetable oil, glycerol, sugar, or the like, but is not limited thereto. These may be used alone or in combination of two or more thereof.

Mode for Invention

EXAMPLE

Hereinafter, the present invention will be described in more detail with reference to examples. However, it will be obvious to those skilled in the art that these examples are provided only for illustration of the present invention, and should not be construed as limiting the scope of the present invention. Accordingly, the substantial scope of the present invention is defined by the appended claims and equivalents thereto.

Example 1

Determination of Optimal Growth Conditions for Each Strain

Growth curves as a function of temperature (25 and 30° C.) and time (2, 4, 6, 8, 10, 12, 14 and 16 days) were plotted for respective strains (*Aspergillus brasiliensis. A. awamori, A. sojae, A. oryzae, Monascus Pilosus, M. Kaoliang*, and *M. Purpureus*) used for chestnut inner shell fermentation according to the present invention, and the results are shown in FIG. 1 below.

As shown in FIG. 1, all four types of strains of *Aspergillus* spp. had a higher growth rate at 25° C. than at 30° C., and mostly grew on the 6th-8th day of fermentation (FIG. 1A), all three strains of *Monascus* spp. had a higher growth rate at 30° C. than at 25° C., and mostly grew on the 10th day of fermentation (FIG. 1B). Based on these results, in the production of fermented chestnut inner shell extract, fermentation using *Aspergillus* spp. was performed at 25° C. for up to 14 days, and fermentation using *Monascus* spp. was performed at 30° C. for up to 22 days.

Example 2

Preparation of Fermented Chestnut Inner Shell Extract

(1) Preparation of Solid Fermented Chestnut Inner Shell Extract

For the preparation of solid fermented chestnut inner shell extract, first, the chestnut inner shell was mixed with water at a ratio of 1:1 (w/v) and sterilized using an autoclave (at 121° C. for 20 minutes). Then, the chestnut inner shell was transferred to a Petri dish and mixed well with spores of 1% *Aspergillus* spp (*A. brasiliensis. A. awamori, A. sojae, A. oryzae*) or 1% *Monascus* spp. (*M. Pilosus, M. Kaoliang*, and *M. Purpureus*). During mixing with *Aspergillus* spp., the mixture was cultured at 25° C. for 14 days at 2-day intervals, and during mixing with *Monascus* spp., the mixture was cultured at 30° C. for 20 days at 2-day intervals.

Next, the fermented chestnut inner shell collected during each culture period was extracted using 95% alcohol at a ratio of 1:10 (w/v), and shaken at 100 rpm, 25° C. for 24 hours. Samples were centrifuged at 3,500 rpm for 15 minutes and filtered. The samples were extracted twice, and the supernatant was collected, evaporated and freeze-dried to prepare a solid fermented chestnut inner shell extract. The prepared solid fermented chestnut inner shell extract was maintained at −20° C. for further analysis.

(2) Preparation of Liquid Fermented Chestnut Inner Shell Extract

For the preparation of the liquid fermented chestnut inner shell extract, first, the chestnut inner shell was mixed with water at a ratio of 1:10 (w/v) and sterilized using an autoclave (121° C. for 20 minutes). Then, each 10% (v/w) *Aspergillus* spp. (*A. brasiliensis. A. awamori, A. sojae, A. oryzae*) or *Monascus* spp. (*M. Pilosus, M. Kaoliang*, and *M. Purpureus*) was added to the mixture, followed by culturing *Aspergillus* spp. at 25° C., and *Monascus* spp. at 30° C. for 20 days at an interval of 2 days.

Next, the fermented chestnut inner shell collected during each culture period was extracted using 95% alcohol at a ratio of 1:10 (w/v), and shaken at 100 rpm, 25° C. for 24 hours. Samples were centrifuged at 3,500 rpm for 15 minutes and filtered. The samples were extracted twice, and the supernatant was collected, evaporated and freeze-dried to prepare a liquid fermented chestnut inner shell extract. The prepared liquid fermented chestnut inner shell extract was maintained at −20° C. for further analysis.

Example 3

Measurement of Total Phenolic Content (TPC)

The total phenolic content (TPC) of the fermented chestnut inner shell extract was determined using a modified method of Ainsworth and Gillespie. Specifically, 200 μl of a 10% (v/v) Folin-Ciocalteu reagent and 800 μl of 700 mM $Na_2CO_3$ were mixed with 100 μl of the fermentation chestnut inner shell extract sample and then the mixture was incubated at room temperature for 2 hours. Then, the absorbance at 765 nm was measured using a spectrophotometer, TPC was calculated using the regression equation of the gallic acid standard curve, and the results are shown in FIGS. 2 to 5 below.

The result of the measurement shows that the fermented chestnut inner shell extract according to the present invention has a higher total phenolic content than the non-fermented general chestnut inner shell extract.

Specifically, the chestnut inner shell extract obtained by solid fermentation for 10 days using *Aspergillus sojae* among *Aspergillus* spp. had a total phenolic content of 39.52 mg GAE/g, which is about 1.6 times higher than that of the unfermented chestnut inner shell extract (25.22 mg GAE/g extract) (FIG. 2A). In addition, the chestnut inner shell extract obtained by liquid fermentation for 10 days using *Aspergillus sojae* among *Aspergillus* spp. had the highest total phenolic content of 44.51 mg GAE/g (FIG. 3A). On the other hand, the chestnut inner shell extracts obtained by fermentation with *A. brasiliensis, A. awamori* and *A. oryzae*, had a decrease in TPC as the fermentation time elapsed, which is considered to be caused by the action of polyphenol oxidase enzymes by the fungus as a single carbon source and the use of phenol (Huang X M. et al., 2005).

Also, the chestnut inner shell extract obtained by solid fermentation for 6 days using *M. Kaoliang* among *Monascus* spp. had a total phenolic content of 63.52 mg GAE/g, which was higher than that of the unfermented chestnut inner shell extract (59.12 mg GAE/g extract) (FIG. 4B) and the chestnut inner shell extract obtained by solid fermentation for 6 days using *M. Purpureus* had a total phenolic content of 41.61 mg GAE/g on the $5^{th}$ to $8^{th}$ day of fermentation (FIG. 4C). In addition, the chestnut inner shell extract obtained by liquid fermentation for 6 days using *M. Kaoliang* had the highest total phenolic content of 110.45 mg GAE/g (FIG. 4C) which corresponds to about 2 times higher than that of the unfermented chestnut inner shell extract (59.12 mg GAE/g extract) (FIG. 5B). In addition, the chestnut inner shell extract obtained by solid fermentation on the $5^{th}$ to $8^{th}$ day using *M. Purpureus* had an increased total phenolic content of 69.11 mg GAE/g (FIG. 5C).

Example 4

Measurement of Antioxidant Activity

The antioxidant activity of the fermented chestnut inner shell extract was determined by measuring 2,2-diphenyl-1-picrylhydrazyl (DPPH) radical scavenging activity. Specifically, 450 μl of 100 mM Tris-HCl buffer (pH 7.4) and 1 ml of 0.1 mM DPPH solution were mixed with 50 μl of the fermented chestnut inner shell extract sample, and then allowed to stand at room temperature for 30 minutes in dark conditions. Then, the absorbance was measured at 517 nm using a spectrophotometer, DPPH radical scavenging activity (%) was calculated using the following Equation 1, and the results are shown in FIGS. 6 to 9 below.

$$DPPH\ \text{radical scavenging activity (\%)}=(\text{blank absorbance}-(\text{sample absorbance}/\text{blank absorbance}))\times 100 \quad \text{[Equation 1]}$$

The result of the measurement showed that the fermented chestnut inner shell extract according to the present invention has improved DPPH radical scavenging activity compared to the non-fermented general chestnut inner shell extract.

Specifically, all of the extracts obtained by solid fermentation using *Aspergillus sojae* among *Aspergillus* spp. exhibited high DPPH radical scavenging activity and the highest DPPH radical scavenging activity of 84.15% on the 8th day of fermentation (FIG. 6A). Solid fermentation using *A. brasiliensis, A. awamori* and *A. oryzae* had behaviors similar to the results of TPC described above (FIGS. 6B, 6C and 6D). Most of extracts obtained by liquid fermentation exhibited higher DPPH radical scavenging activity than the unfermented extract, except on the 12th day of fermentation (FIG. 7A).

Also, the extract obtained by solid fermentation using *M. Kaoliang* among *Monascus* spp. had the highest DPPH activity of 51.98% on the 3$^{rd}$ day of fermentation (FIG. 8B). In addition, the extract obtained by liquid fermentation using *M. Pilosus* exhibited the highest DPPH activity of 65% on the 7.5$^{th}$ day of fermentation, which corresponds to about 1.5 times higher than that of the unfermented extract (48.44%) (FIG. 9A). The extract obtained by fermentation using *M. Kaoliang* exhibited the highest DPPH activity of 68.97% on the 3$^{rd}$ day of solid fermentation (FIG. 9B).

Example 5

Measurement of Whitening Activity

The whitening activity of the fermented chestnut inner shell extract was determined by measuring the tyrosinase inhibition activity. Specifically, 40 μl of the fermented chestnut inner shell extract sample dissolved in 40 μl of tyrosinase (240 U/ml) of pH 6.5 was mixed with 80 μl of 50 mM potassium phosphate buffer (P-buffer) in 5% DMSO, the mixture was incubated at 25° C. for 10 minutes, and 40 μl of 0.85 mM L-3,4-dihydroxyphenylalanine (L-DOPA) was added thereto. Then, the mixture was continuously incubated at 25° C. for 5 minutes, and absorbance was measured at 490 nm using a microplate spectrophotometer (Bio-Tek). 0.2 mg/ml of Kojic acid was used as a positive control, the tyrosinase inhibition activity (%) was calculated in accordance with the following Equation 2, and the results are shown in FIGS. 10 to 13 below.

$$\text{Tyrosinase inhibition activity (\%)}=(((A-B)-C-D))/(A-B))\times 100 \quad \text{[Equation 2]}$$

A=blank sample containing tyrosinase

B=blank sample not containing tyrosinase

C=sample containing tyrosinase

D=sample not containing tyrosinase

The result of the measurement showed that the fermented chestnut inner shell extract according to the present invention had improved tyrosinase inhibitory activity compared to the non-fermented general chestnut inner shell extract.

Specifically, regarding fermentation with *A. sojae* among *Aspergillus* spp., the extracts obtained by both solid fermentation and liquid fermentation had higher tyrosinase inhibitory activity than unfermented extracts except on the 2$^{nd}$ day of fermentation, and the fermented extracts on the 6$^{th}$ to 10$^{th}$ day had a high inhibitory activity of about 90% or more (FIGS. 10A and 11A). In addition, the fermented extract obtained using *A. brasiliensis* was found to exhibit improved inhibitory activity on the 6$^{th}$ and 8$^{th}$ days of fermentation (FIGS. 10B, 10C and 10D).

Also, the extract obtained by solid fermentation using *M. Kaoliang* among *Monascus* spp. had tyrosinase inhibitory activity of 54.11% on the 6$^{th}$ day of solid fermentation, which was about 5 times higher than that of the unfermented extract (11.74%) (FIG. 12B). The extract obtained by liquid fermentation using *M. Pilosus* exhibited tyrosinase inhibitory activity of 85.71% on the 7.5$^{th}$ day of liquid fermentation, which was about 8.5 times higher than that of the unfermented extract (9.63%) (FIG. 13A). The extract obtained by solid fermentation using *M. Kaoliang* exhibited the highest tyrosinase inhibitory activity of 68.12% on the 12$^{th}$ day of fermentation (FIG. 13B).

Example 6

Measurement of Wrinkle Amelioration Activity

The wrinkle amelioration activity of the fermented chestnut inner shell extract was determined by measuring the elastase inhibition activity. Specifically, 30 μl of the fermented chestnut inner shell extract sample was mixed with 100 μl of 2 mM Tris buffer (pH 8.0) and 10 μl of elastase (1.1 U/ml), followed by incubation at 25° C. for 10 minutes, and addition of 40 μl of 3 mg/ml N-Succ-Ala-Ala-Ala-p-nitroanilide (SANA). The mixture was continuously incubated at 25° C. for 20 minutes, and absorbance was measured at 410 nm using a microplate spectrophotometer (Bio-Tek). 0.2 mg/ml of oleanolic acid was used as a positive control, the elastase inhibitory activity (%) was calculated in accordance with the following Equation 3, and the results are shown in FIGS. 14 to 17 below.

$$\text{Elastase inhibitory activity (\%)}=(((A-B)-(C-D))/(A-B))\times 100 \quad \text{[Equation 3]}$$

A=blank sample containing elastase

B=blank sample not containing elastase

C=sample containing elastase

D=sample not containing elastase

The result of the measurement showed that the fermented chestnut inner shell extract according to the present invention exhibited improved elastase inhibitory activity compared to the non-fermented general chestnut inner shell extract.

Specifically, the extract obtained by solid fermentation using *A. sojae* among *Aspergillus* spp. had elastase inhibitory activity of 83.01% on the 8$^{th}$ day of solid fermentation (FIG. 14A), and the highest elastase inhibitory activity of 90.46% on the 8$^{th}$ day of liquid fermentation (FIG. 15A). The extract obtained by fermentation using *A. awamori* exhibited greatly improved elastase inhibitory activity of 87.72% on the 10$^{th}$ day of fermentation, compared to the non-fermented general chestnut inner shell extract (22.06%) (FIGS. 14A, 14B, 14C and 14D).

Also, the extract obtained on the 3$^{rd}$ day of solid fermentation by solid fermentation using *M. Kaoliang* among *Monascus* spp. exhibited elastase inhibitory activity of 73.29%, which was 10% higher than that of the non-fermented general chestnut inner shell extract (64.02%) (FIG. 16), the extract obtained on the 16$^{th}$ day of solid fermentation by solid fermentation using *M. Purpureus* exhibited elastase inhibitory activity of 27.77%, and the extract obtained on the 3$^{rd}$ day of liquid fermentation by liquid fermentation using *M. Purpureus* exhibited the highest elastase inhibitory activity of 79.85% (FIG. 17B). The extract obtained on the 5$^{th}$ day of liquid fermentation by liquid fermentation using *M. Pilosus* exhibited elastase inhibitory activity of 24.44% (FIG. 17A).

Example 7

Identification of Bioactive Substances

According to the present invention, the profile of bioactive substances contained in the extracts fermented using *Aspergillus sojae* and *Monascus Kaoliang* was determined using HPLC analysis. Specifically, each fermented chestnut inner shell skin extract sample was filtered through a 0.2 μm filter, HPLC analysis was performed using DIONEX UltiMate 3000 (Thermo Scientific, CA, USA), and a reversed-phase Acclaim™ 120 C18 (5 μm) column (4.6×250 mm, Thermo Scientific, CA, USA). The mobile phase was a gradient of 0.05% phosphoric acid (solution A) and acetonitrile (solution B). The gradient program is as follows (0 min, 0% B; 10 min, 7% B; 20 min, 10% B; 30 min, 12% B; 50 min, 23% B; 70 min, 35% B; 80 min, 50% B; 90 min, 0% B. The flow rate was 0.5 ml/min). The temperature was set to 40° C., the UV detection wavelengths at 280, 320 and 360 nm were measured using UV-Vis detectors, and the results are shown in Tables 1 and 2 below, respectively.

TABLE 1

| Sample | Kojic acid (mg/g extract) | Gallic acid (μg/g extract) | Ellagic acid (μg/g extract) | Coumaric acid (μg/g extract) | Ferulic acid (μg/g extract) | Sinapic acid (μg/g extract) |
|---|---|---|---|---|---|---|
| Native | ND | 1389.75 ± 25.96$^{d}$ | ND | ND | 71.03 ± 4.14$^{a}$ | 24.99 ± 4.01$^{c}$ |
| Fermented* | 49.97 ± 0.12$^{a}$ | 5616.22 ± 23.99$^{b}$ | 330.17 ± 9.61$^{a}$ | 21.34 ± 0.05$^{a}$ | 71.08 ± 0.03$^{a}$ | 145.65 ± 0.08$^{a}$ |

Different alphabets were different with statistical significance ($p < 0.05$).
*Chestnut inner shell extract obtained by solid fermentation for 10 days with *A. sojae*.
** ND, not detected As can be seen from Table 1, from the chestnut inner shell extract fermented with *Aspergillus sojae*, about 50 mg/g of kojic acid, which does not exist in the natural chestnut inner shell, was detected, which is considered to improve the tyrosinase inhibitory activity. In addition, it was confirmed that phenolic acids (gallic acid, ellagic acid, coumaric acid, ferulic acid, and sinapic acid) were newly detected or the contents thereof were greatly increased by fermentation with *Aspergillus sojae*.

TABLE 2

| Sample | Gallic acid (μg/g fermented dry sample) | Ellagic acid (μg/g fermented dry sample) | Syringic acid (μg/g fermented dry sample) |
|---|---|---|---|
| Native | 186.368 | 151.982 | 4.889 |
| Solid State* Fermentation | ND | 201.351 | 50.835 |
| Liquid State** Fermentation | 362.15 | 365.073 | 11.004 |

Different alphabets were different with statistical significance ($p < 0.05$).
*Chestnut inner shell extract obtained by solid fermentation for 9 days with *M. kaoliang*.
**Chestnut inner shell extract obtained by liquid fermentation for 6 days with *M. kaoliang*.
*** ND, not detected As can be seen from Table 2, phenolic acids such as gallic acid, ellagic acid, and sinapic acid were newly detected from the chestnut inner shell extract fermented with *Monascus kaoliang*, or the contents thereof were greatly increased.

Although specific configurations of the present invention have been described in detail, those skilled in the art will appreciate that this detailed description is provided as preferred embodiments for illustrative purposes and should not be construed as limiting the scope of the present invention. Therefore, the substantial scope of the present invention is defined by the accompanying claims and equivalents thereto.

INDUSTRIAL APPLICABILITY

The composition according to the present invention is useful as a cosmetic composition due to excellent antioxidant, skin-whitening and anti-wrinkle activities thereof.

The invention claimed is:

1. A topical cosmetic composition comprising a fermented chestnut inner shell extract or fraction thereof as active ingredient, wherein the fermented chestnut inner shell extract is obtained by solid fermentation of the chestnut inner shell by inoculation with *Aspergillus sojae*, followed by fermentation and extraction, wherein the fermentation is performed for 10 days by culturing the chestnut inner shell at 25° C., and wherein the composition comprises kojic acid, gallic acid, ellagic acid, coumaric acid, ferulic acid, and sinapic acid.

2. The topical cosmetic composition according to claim 1, wherein the fermentation is performed by inoculating 0.1 to 20 parts by weight of the *Aspergillus sojae* with respect to 100 parts by weight of the chestnut inner shell.

3. The topical cosmetic composition according to claim 1, wherein the fermented chestnut inner shell extract is obtained by extraction using at least one extraction solvent selected from the group consisting of water, C1-C4 anhydrous or hydrous alcohol, ethyl acetate, acetone, glycerin, ethylene glycol, propylene glycol and butylene glycol.

4. The topical cosmetic composition according to claim 1, wherein the fraction is obtained by fractionating the fermented chestnut inner shell extract with a solvent selected from the group consisting of hexane, chloroform, ethyl acetate, butanol, water, and a mixture thereof.

5. The topical cosmetic composition according to claim 1, wherein the cosmetic composition is for antioxidant, skin-whitening or wrinkle-amelioration application.

6. The topical cosmetic composition according to claim 1, wherein the composition has a formulation selected from the group consisting of a solution, external ointment, cream, foam, nourishing lotion, softening lotion, pack, softening water, serum, makeup base, essence, soap, liquid detergent, bath agent, sunscreen cream, sun oil, suspension, paste, gel, surfactant-containing cleanser, oil, powder foundation, emulsion foundation, wax foundation, patch and spray.

7. A topical cosmetic composition comprising a fermented chestnut inner shell extract or fraction thereof as active ingredient, wherein the fermented chestnut inner shell extract is obtained by liquid fermentation of the chestnut inner shell by inoculation with *Monascus kaoliang*, followed by fermentation and extraction, and wherein the fermentation is performed for 6 days by culturing the chestnut inner shell at 30° C., and wherein the composition comprises gallic acid, ellagic acid, and syringic acid.

8. The topical cosmetic composition according to claim 7, wherein the fermentation is performed by inoculating 0.1 to 20 parts by weight of the *Monascus* spp. strains with respect to 100 parts by weight of the chestnut inner shell.

9. The topical cosmetic composition according to claim 7, wherein the fermented chestnut inner shell extract is obtained by extraction using at least one extraction solvent selected from the group consisting of water, C1-C4 anhydrous or hydrous alcohol, ethyl acetate, acetone, glycerin, ethylene glycol, propylene glycol and butylene glycol.

10. The topical cosmetic composition according to claim 7, wherein the fraction is obtained by fractionating the fermented chestnut inner shell extract with a solvent selected from the group consisting of hexane, chloroform, ethyl acetate, butanol, water, and a mixture thereof.

11. The topical cosmetic composition according to claim 7, wherein the cosmetic composition is for antioxidant, skin-whitening or wrinkle-amelioration application.

12. The topical cosmetic composition according to claim 7, wherein the composition has a formulation selected from the group consisting of a solution, external ointment, foam, nourishing lotion, softening lotion, pack, softening water, serum, makeup base, essence, soap, liquid detergent, bath agent, sunscreen cream, sun oil, suspension, paste, gel, surfactant-containing cleanser, oil, powder foundation, emulsion foundation, wax foundation, patch and spray.

* * * * *